United States Patent
Fish et al.

(10) Patent No.: US 6,716,596 B2
(45) Date of Patent: Apr. 6, 2004

(54) AGENTS FOR REPLACEMENT OF NAD+/NADH SYSTEM IN ENZYMATIC REACTIONS

(75) Inventors: Richard H. Fish, Berkeley, CA (US); John B. Kerr, Oakland, CA (US); Christine H. Lo, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/805,726

(22) Filed: Mar. 12, 2001

(65) Prior Publication Data

US 2003/0022266 A1 Jan. 30, 2003

(51) Int. Cl.⁷ ................................................. C12Q 1/26
(52) U.S. Cl. .......................................... 435/25; 435/26
(58) Field of Search ................................. 435/25, 26, 4

(56) References Cited

U.S. PATENT DOCUMENTS 5,801,006 A * 9/1998 Kaufman

OTHER PUBLICATIONS

Lo, H. Bioorganometallic Chemistry. Inorg Chem 2001 40(26)6705–6716.*
Lo, H. Regioselective Reduction of NAD+Models . . . Angew Chem Int Ed 199 38(10)1429–1432.*
Willner I. Thermal and Photochemical Regeneration of Nicotinamide Cofactors . . . J Chem Soc, Perkin Trans 2, 1990 Vol. 4, 559–564.*
Friedlos et al. (1992). Identification of novel reduced pyridinium derivatives as synthetic co–factors for the enzyme DT diaphorose NAD(P)H dehydrogenase. Biochemical Pharmacology 44 (1): 25–31.*

Maria Miller, et al., 482–Red–Ox Transformations of NAD+ Model Compounds, *Bioelectrochemistry and Bioenergetics*, 9:287–298 (1982).
Adam Heller, Electrical Wiring of Redox Enzymes, *Acc. Chem. Res.*, 23:128–134 (1990).
A. S. Paxinos, et al., Direct Electron Transfer From Modified Glassy Carbon Electrodes Carrying Covalently Immoblixed Mediators to a Dissolved Viologen Accepting Pyridine Nucleotide Oxidoreductase and Dihydrolipoamide Dehydrogenase, *Bioelectrochemistry and Bioenergetics*, 12:425–436 (1991).
Dariusch Hekmat, et al., Production of Pyruvate from (R)–lactate in an Enzyme–Membrane Reactor with Coupled Electrochemical Regeneration of the Artifical Mediator Anthraquinone–2,6–disulfonate, *Enzyme and Microbial Technology*, 24:471–479 (1999).
Eva Höfer, et al., Polymer–Modified Electrodes with Pendant [$Rh^{III}(C_5Me_5)$ (L)Cl]+—complexes Formed by γ–irridiation Cross–Linking, *Journal of Electroanalytical Chemistry*, 402:115–122 (1996).
Richard J. Ansell, et al., Synthesis and Properties of New Coenzyme Mimics Based on the Artifical Coenzyme CL4, *J. Mol. Recognit.*, 12:45–56 (1999).

* cited by examiner

Primary Examiner—Ralph Gitomer
(74) Attorney, Agent, or Firm—Hana Verny

(57) ABSTRACT

Novel agents acting as co-factors for replacement of NAD(P)+/NAD(P)H co-enzyme systems in enzymatic oxidoreductive reactions. Agents mimicking the action of NAD(P)+/NAD(P)H system in enzymatic oxidation/reduction of substrates into reduced or oxidized products. A method for selection and preparation of the mimicking agents for replacement of NAD(P)+/NAD(P)H system and a device comprising co-factors for replacement of NAD(P)+/NAD(P)H system.

18 Claims, 7 Drawing Sheets

R=-C(O)NH$_2$ (1a);
-C(O)NHCH$_3$ (1b);
-C(O)N(C$_2$H$_5$)$_2$ (1c);
-C(S)NH$_2$ (1d);
-C(O)CH$_3$ (1e);
-C(O)CCH$_3$ (1f);
-CN (1g);
-CH$_3$ (1h);
-H (1i)

(1)

| substrate | R | relative rate[A] | turnover/h[B] |
|---|---|---|---|
| 1a | $\underset{NH_2}{\overset{O}{\unicode{x2A}}}$ | 1.0 | 8 |
| 1b | $\underset{NHCH_3}{\overset{O}{\unicode{x2A}}}$ | 0.9 | 8 |
| 1c | $\underset{NEt_2}{\overset{O}{\unicode{x2A}}}$ | 0.0 | 0 |
| 1d | $\underset{NH_2}{\overset{S}{\unicode{x2A}}}$ | 1.3 | 11 |
| 1e | $\underset{CH_3}{\overset{O}{\unicode{x2A}}}$ | 1.1 | 9 |
| 1f | $\underset{OCH_3}{\overset{O}{\unicode{x2A}}}$ | 1.3 | 11 |
| 1g | −CN | 0.9 | 8 |
| 1h | −CH₃ | 0.0 | 0 |
| 1i | −H | 0.0 | 0 |

FIG. 2A
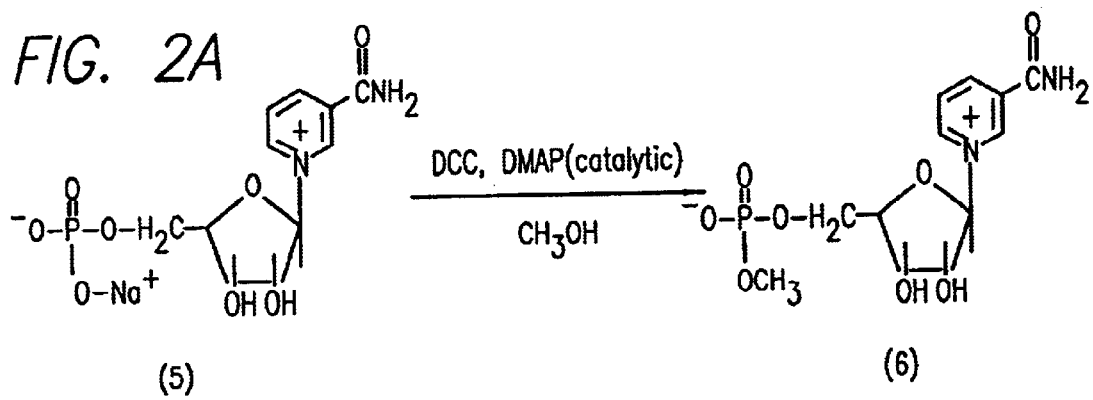
FIG. 2B
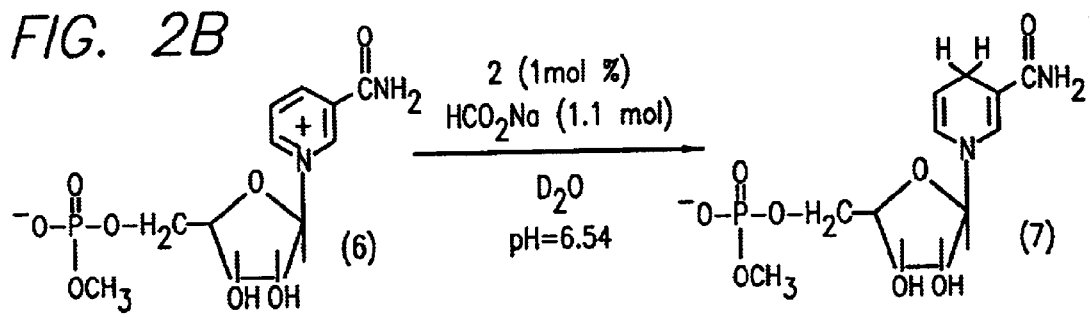
FIG. 3
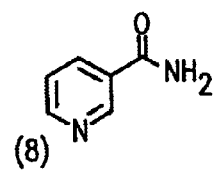
(8)
+
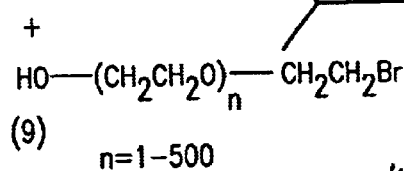
(9) n=1-500
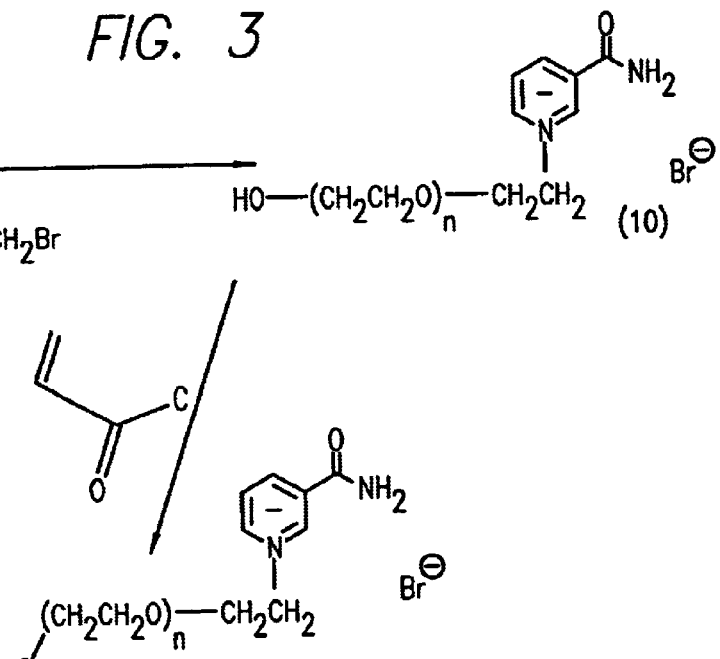

Enzymatic Reductions of Ketones with NAD$^+$ Models:
Turnover Frequencies and Enantiomeric Excess[a,b]

| substrate | | product | % yield | TOF(d$^{-1}$) | ee (%,S) |
|---|---|---|---|---|---|
| PhCH$_2$CH$_2$C(O)CH$_3$ | 12 | PhCH$_2$CH$_2$C(OH)(H)-CH$_3$ | 90(91) | 30(31) | 93(93) |
| PhCH$_2$C(O)CH$_3$ | 13 | PhCH$_2$C(OH)(H)-CH$_3$ | 55(59) | 18(19) | >99(99) |
| PhC(O)CH$_3$ | 14 | Ph-C(OH)(H)-CH$_3$ | 5(5) | 4(4) | >96(96) |
| H$_3$C-CH$_2$-C(O)-CH$_3$ | 15 | H$_3$C-CH$_2$-C(OH)(H)-CH$_3$ | 41(59) | 14(20) | 85(85)[c] |

[a]The results from NAD$^+$ were given in parenthesis. [b]The enantiomeric excess was determined by GLC with a modified β-cyclodextrin capillary column. [c]Based on derivatization with an optically pure isocyanate.

FIG. 7

AGENTS FOR REPLACEMENT OF NAD+/NADH SYSTEM IN ENZYMATIC REACTIONS

This invention was supported by research grants with the U.S. government support under Contract No. DE-AC03-76SF00098 between the U.S. Department of Energy and the University of California for the operation of Lawrence Berkeley National Laboratory (LBNL). The U.S. Government may have certain rights in the invention.

BACKGROUND OF THE INVENTION

1. Field of the Invention

This invention concerns novel agents acting as co-factors for replacement of NAD(P)⁺/NAD(P)H co-enzyme systems in enzymatic oxido-reductive reactions. In particular, the invention concerns water soluble or partially water soluble agents mimicking the action of NAD(P)⁺/NAD(P)H system in enzymatic oxidation/reduction of substrates into reduced or oxidized products. The invention further concerns a method for selection and preparation of the mimicking agents for replacement of NAD(P)⁺/NAD(P)H system. Finally, the invention concerns a device comprising co-factors for replacement of NAD(P)⁺/NAD(P)H system.

2. Background and Related Disclosures

Due to their high selectivity and low environmental impact, enzymatic reactions are critically important. More than 35% of all known enzymes, however, need coenzymes or co-factors to enable their proper function. In particular, oxido-reductases, enzymes which catalyze oxidation and/or reduction of a substrate to a product, require the regeneration of NAD(P)⁺ and NAD(P)H co-factors for energy delivery. However, the utility of NAD(P)⁺/NAD(P)H oxido-reduction system for industrial purposes is impractical because the endogenous supply of NAD⁺/NADH co-factors is limited, and recovery of these co-factors from the natural sources or their synthetic preparation is expensive. Moreover, the energy delivery to the NAD(P)⁺/NAD(P)H regeneration processes requires redox catalysts and, therefore, the regiospecific regeneration of NAD(P)H at high rates is necessary. Such co-factor regeneration has been the limiting step for the economic utilization of NAD(P)⁺/1,4-NAD(P)H system in enzymatic chiral synthesis reactions, particularly for larger volume and more energy intensive processes.

Development of practical methods for the regeneration of the co-enzyme 1,4-NADH, the reduced form of nicotinamide adenine dinucleotide (NAD⁺), has continued to be of significant importance in the biocatalysts field, where enzymatic reduction reactions are used for chiral organic compound synthesis (*Appl. Biochem. Biotech.*, 14:147 (1984) and *J. Chem. Soc. Perkin Trans.*, 1:967 (1995)).

Conversion of NAD₊ to 1,4-NADH by enzymatic, chemical, photochemical, or electrochemical methods has been extensively studied.

In order to develop faster rates and a more economical regeneration process, various transition metal hydrides have been studied as catalysts for the regioselective reduction of NAD⁺ and NAD⁺ models to the 1,4-NADH derivatives as described in *Organometallics*, 10:1568 (1991), *J. Am. Chem. Soc.*, 116:2141 (1994) and *Nat. Struct. Biol.*, 3:213 (1996)).

In the most illustrative example, *Angew. Chem. Int. Ed. Engl.*, 29:388 (1990), describes the use of in situ generated [Cp*Rh(bpy)(H)]+(bpy=2,2'-bipyridyl), for the regiospecific reduction of NAD⁺ to 1,4-NADH, and then demonstrated the co-factor regeneration process with enzymatic, chiral reduction reactions.

While the above mentioned reduction of NAD⁺ by [Cp*Rh(bpy)H]⁺ was shown, at that time, to be highly regiospecific for 1,4-NADH, the mechanistic details of this important co-factor conversion were not known (*Chem. Ber.*, 122:1869 (1989) and *Orcanometallics* (1991), supra). Some insights were only recently provided by inventors in a preliminary communication published in *Angew. Chem. Int. Ed.*, 38:1429 (1999).

The above described methods were used solely for regeneration of the overly expensive NAD⁺/NADH system which is not suitable for larger volume and more energy intensive oxido-reductive enzymatic processes. For these purposes, the industrial utilization of NAD(P)⁺/NAD(P)H system is limited.

Therefore, it would be highly advantageous to have available new methods and/or agents which would replace expensive NAD(P)⁺/NAD(P)H system. Such methods and/or agents for complete replacement for NAD(P)⁺/NAD(P)H would greatly increase the capacity of enzymatic oxido-reduction reactions to deal with large volumes of products.

It is, therefore, a primary objective of the current invention to provide effective and inexpensive agents acting as co-factors for replacement of the NAD⁺/NADH system in oxidation/reduction enzymatic reactions and a method of use thereof.

All patents, patent applications and publications cited herein are hereby incorporated by reference.

SUMMARY

One aspect of the current invention is a method for effective replacement of NAD(P)⁺/NAD(P)H system in enzymatic oxido-reductive reactions with novel agents of the invention.

Another aspect of the current invention is a method for replacement of NAD(P)⁺/NAD(P)H system in enzymatic oxido-reduction reactions comprising replacing the NAD(P)⁺/NAD(P)H with novel water soluble or partially water soluble agents acting as co-factors for oxido-reduction reactions and mimicking the action of NAD(P)⁺/NAD(P)H system.

Still yet another aspect of the current invention concerns a group of novel agents acting as co-factors for replacement and closely mimicking the action of NAD(P)⁺/NAD(P)H system in oxido-reduction enzymatic reactions, said agents depicted by the formula

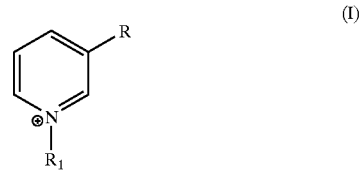

(I)

wherein R is —CN, —C(O)NH₂, —C(O)NHCH₃, —C(O)N(C₂H₅), —C(S)NH₂, —C(O)CH₃, or —C(O)OCH₃;

wherein R₁ is —(CH₂(CH₂O)ₙYR₂, ribose-Y—R₂, or

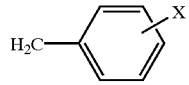

wherein Y is —OPOO—, —OBO₂—, —OSO₂—, CH₃NH—, —(CH₂)ₙNH—, adenine, or imidazole;

wherein $R_2$ is H, —$CH_3$, —$(OCH_2CH_2)_n$, —$(NCH_2CH_2)_n$— or —$[(N=P(OCH_3)_2]_n$;

wherein X is —$OCH_3$, —$CF_3$, —$O(CH_2CH_2O)_n$ or —$OPOOR_2$;

wherein $R_3$ is H, —$CH_3$, —$(OCH_2CH_2)_n$, —$(NCH_2CH_2)_n$— or —$[N=P(OCH_3)_2]_n$; and wherein n is 1–2000; or a salt thereof.

Yet another aspect of the current invention concerns novel water soluble, or partially water soluble biomimics suitable for replacement of NAD(P)$^+$/NAD(P)H system in reductive enzymatic reactions represented by N-substituted nicotinamide compounds and structurally related compounds and their derivatives chemically reduced by a catalyst formed by a reaction of a rhodium compound [Cp*Rh(bipyridyl)H]$^+$ or other metal comprising compound with a reducing agent, said compounds functioning as co-factors for replacement of NAD(P)$^+$/NAD(P)H system.

Yet another aspect of the current invention concerns novel water soluble, or partially water soluble biomimics suitable for replacement of NAD(P)$^+$/NAD(P)H system in reductive enzymatic reactions represented by β-nicotinamide ribose-5'-methyl phosphate and structurally related compounds and their derivatives chemically reduced by a catalyst formed by a reaction of a rhodium compound ~Cp*Rh(bipyridyl)H]$^+$ or other metal comprising compound with reducing agents, said compound functioning as co-factors for replacement of NAD(P)$^+$/NAD(P)H system.

Yet another aspect of the current invention concerns novel water soluble, or partially water soluble biomimics suitable for replacement of NAD(P)$^+$/NAD(P)H system in oxidative enzymatic reaction by N-substituted nicotinamide compounds that are oxidized by electrodes, photons, chemical oxidants or enzymes.

Yet another aspect of the current invention concerns novel water soluble, or partially water soluble biomimics suitable for replacement of NAD(P)$^+$/NAD(P)H system in oxidative enzymatic reaction by β-nicotinamide ribose-5' methyl phosphate nicotinamide compounds that are oxidized by electrodes, photons, chemical oxidants or enzymes.

Still yet another aspect of the current invention is a device, such as a biosensor or a chemical membrane bioreactor, useful for replacement and/or regeneration of NAD(P)$^+$/NAD(P)H system.

BRIEF DESCRIPTION OF THE FIGURES

FIG. 2A shows a chemical synthesis of the compound β-nicotinamide ribose-5'-methyl phosphate (6), an aqueous biomimetic with structural characteristics closely mimicking the natural NAD(P)$^+$, from a commercially available precursor, β-nicotinamide ribose-5'-phosphate (5) via a methylation reaction using dicyclohexylcarbodiimide (DCC) and a catalytic amount of p-dimethylaminopyridine (DMAP) in methanol. FIG. 2B illustrates reduction reaction of β-nicotinamide ribose-5'-methyl phosphate (6) into its 1,4-dihydro derivative (7).

FIG. 3 shows a chemical structure and a synthetic preparation of a second generation of water soluble biomimics, incorporated into polymeric matrices (11) to provide devices for replacement of the NAD(P)+/NAD(P)H system with biomimic easily separated from the enzyme system.

FIG. 4 also illustrates transfer of electrons from chemicals, such as hydride transfer agents, photons or electrodes to the enzyme redox center via the reduction of biomimics into their reductive derivatives.

FIG. 6 further illustrates biomimetic regeneration of co-enzymes, enzyme recognition and chiral synthesis of alcohols.

FIG. 7 illustrates enzymatic reductions of ketones into their chiral alcohols with biomimics of the invention.

DEFINITIONS

Figure 1A:
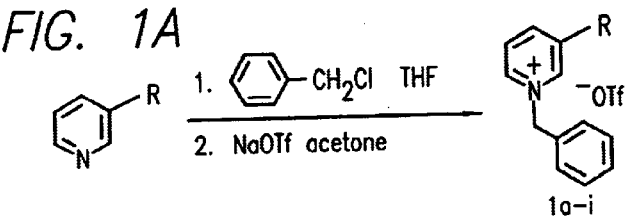
FIG. 1A shows a chemical synthesis of 1-benzylpyridinium (1) substituted with a variety of R-substituents on 3-position.

As described herein:

"Agent", "biomimetic agent", "biomimetic compound", "biomimic" or "co-factor" means a compound which acts as a co-factor for oxido-reduction reaction and effectively mimics the action of and replaces NAD(P)$^+$/NAD(P)H system.

"NAD$^+$" means oxidized form of nicotinamide adenine dinucleotide.

"NAD$^+$ model" means a compound possessing regiospecific, stereospecific and/or chemospecific properties similar or equal to NAD$^+$.

"NADH" means reduced form of nicotinamide adenine dinucleotide, the hydride donor in enzymatic reactions.

"NADP$^+$/NADPH" means oxidized (NADP$^+$) or reduced (NADPH) nicotinamide adenine nucleotide phosphate.

"NAD(P)$^+$/NAD(P)H" means and includes both oxidized NAD$^+$ and NADP$^+$ and reduced NADH and NADPH forms.

"Co-factor" means a chemical substance, molecule or atom essential for the action of another molecule. The co-factor acts in accord with the other molecule to bring about certain effects. For example, a co-factor may enable action of a catalyst in the chemical reaction or, as in this instance, a co-factor enabling oxidative/reductive enzymatic reaction. The co-factor is sometimes called "co-enzyme".

"Stereoselective" means a process in which of the two or more possible stereoisomeric products only one predominate.

"Regioselective" means a process in which of the two or more regioselective products only one predominates, such as, for example, 1,4-product versus 1,6-product.

"Redox" means chemical reaction comprising oxidation and reduction.

"HLADH" means horse liver alcohol dehydrogenase.

"Oxidoreductase" means an enzyme which catalyzes oxidation-reduction reactions.

"Precatalyst" or "catalyst precursor" means a compound, such as [Cp*Rh(bpy)(H$_2$O)], which is converted to the catalyst with sodium formate to [Cp*Rh(bpy)H]$^+$ in a 3-hydrogen elimination. Typically, the precatalyst is a compound comprising rhodium, zinc, cobalt, nickel, ruthenium, iridium and such others.

"1-Benzylnicotinamide" means 3-amidopyridinium.

"TOF" means a turnover frequency in the regioselective reduction, that is, the number of oxidation/reduction cycles completed per hour.

"[Cp*Rh(bpy)H]$^+$" means a rhodium hydride produced from the catalyst precursor, wherein "bpy" means 2,2'bipyridyl.

"Salt" means chloride bromide, phosphate, sulfate, nitrate, perchlorate, tetrafluoroborate, triflate and such other commonly used salts.

DETAILED DESCRIPTION OF THE INVENTION

The invention described herein concerns a group of novel biomimetic compounds which mimic a function of NAD(P)$^+$/NAD(P)H system in oxido-reduction reactions and function as co-factors for oxido-reduction reactions thereby replacing the endogenous NAD(P)$^+$/NAD(P)H system.

The invention further concerns a method of use of these biomimics in biocatalytic oxidative/reductive processes replacing NAD(P)$^+$/NAD(P)H system.

Additionally, the invention provides a method for designing, selecting and preparing these biomimics as well as biosensors or chemical membrane bioreactor devices comprising the biomimic agents of the invention and permitting the use of the biomimics of the invention for regeneration of the redox system, whether such system be NAD(P)$^+$/NAD(P)H or a system comprising novel biomimics.

Novel biomimics of the invention are both water or partially water and organic solvent soluble for both oxidized and reduced forms and possess many similar chemical and physical attributes of NAD$^+$, NADP$^+$, 1,4-NADH or 1,4-NADPH. The novel biomimics are useful as biomimetic compounds for effective and inexpensive replacement of NAD(P)$^+$/NAD(P)H system in oxidative/reductive reactions and may be also useful in regeneration processes of the NAD(P)$^+$/NAD(P)H system which, by itself, is rate limiting and, therefore, uneconomical and impractical.

During the development of this invention, the oxidative/reductive enzymatic system and a function of NAD(P)$^+$/NAD(P)H therein, as well as possible replacement and/or regeneration of NAD(P)$^+$/NAD(P)H system with novel biomimetics in enzymatic reaction, was investigated.

I. Enzymes and NAD(P)$^+$/NAD(P)H system

Enzymes are biological catalysts which participate in many chemical reactions occurring in living organisms. Enzymes catalyze various reactions under mild physiological conditions in neutral aqueous solutions, at normal temperature and pressure and at normal pH. The enzymes are of special value for organic synthesis due to their high chemo-regio-stereo selectivity. Enzymes catalyze enzymatic conversion of substrates to products with high specificity.

Typically, the enzymes require for their activity a presence of co-factors, also called co-enzymes, that enhance the reaction or are necessary for the action of the enzyme.

One of the most important enzymatic systems is oxido-reduction enzymatic conversion. Such enzymatic conversion requires so called "co-factors" which accept and transfer hydrogen. Two of the most important co-factors of oxidative/reductive enzymatic reactions are NAD$^+$ or NADP$^+$ (oxidized form of nicotinamide adenine dinucleotide or a phosphate thereof) and NADH or NADP$^+$ (reduced form of nicotinamide adenine dinucleotide or a phosphate thereof) typically found in 1,4-NADH or 1,4-NAD(P)H forms. These two co-factors form a NAD(P)$^+$/NAD(P)H system in which, during-each oxidation reaction, NAD(P)$^+$ accepts hydrogen from the reduced product or, during the reduction, NADPH donates hydrogen to the substrate by converting NADH to NAD$^+$. The oxidation/reduction reaction in the NAD(P)$^+$/NAD(P)H system in a simplest form is illustrated by the equation NAD$^+$+H$^-$=NADH.

Co-factors are very important components of enzymatic reactions and large number of all known enzymes, particularly those involved in redox reactions, require their presence. The amount and availability of the co-factors are often rate limiting.

II. Requirements for regeneration or replacement of NAD(P)$^+$/NAD(P)H system with novel biomimics Requirement for oxido-reduction co-factor regeneration or replacement process are very stringent.

Regeneration or replacement of the NAD(P)$^+$/NAD(P)H system requires that a specific hydride source is provided during regeneration process.

For example, during oxidation of alcohol (substrate) into ketone (oxidized product) the NAD(P)$^+$ co-factor accepts a hydride to permit oxidation of the substrate into the oxidized product by oxidase. During this process, NAD(P)$^+$ accepts a hydride and at the end of this reaction, NAD(P)$^+$ is converted into its reduced form NAD(P)H. In order to enable the oxidase enzyme to repeat the same reaction, that is, another oxidation, NAD(P)H must be converted back into NAD(P)$^+$. This conversion happens when the enzymatic reaction proceeds in the other direction, that is, when the oxidized substrate is reduced into the reduced product. If such is not the case, the oxidative processes are necessarily limited by the amount of available NAD(P)$^+$.

NADH molecule exists in three regio or positional isomeric forms, namely as 1,4-NADH, 1,2-NADH and 1,6-NAPH stereoisomers, however, only the 1,4-regioisomer is enzymatically active. Any compound replacing the NAD$^+$ and 1,4-NADH co-factors must possess the same or similar properties as NAD$^+$ or 1,4-NADH.

Replacement of co-factors NAD(P)$^+$/NAD(P)H requires that the replacing co-factors take place of NAD(P)$^+$/NAD(P)H and function in substantially the same way, that is, that they are able to transfer hydrogen back and forth.

Both reduction and oxidation must take place under conditions that are compatible with the enzymes, substrates, products and the co-factors themselves. Acid-base hydrolysis reactions can lead to irreversible inactivation of the co-factors as well as the enzyme catalysts and therefore, pH conditions must be the same or similar to those present under physiological or enzyme reactive conditions to prevent co-factor deactivation.

The conditions for redox reaction must also be maintained. The enzyme redox system requires a catalyst precursor which facilitates hydride transfer to and from the enzyme redox center. In this regard, metal complexes, such as rhodium, iridium, zinc, cobalt, ruthenium, nickel, exemplarized by the [Cp*Rh(bpy)(H$_2$O)](OTf)$^{2+}$ complex, have been shown to have the best reaction rates, the correct regiospecificity, and are the least prone to deactivation due to reaction with the medium.

High efficiency is also required in such regeneration or replacement, otherwise the enzymatic reaction will rapidly cease. There should be no side reactions of co-factors with any of the reaction agents used for regeneration. There should be no reactivity of the co-factor with the substrates, products or enzymes. There should be no reaction or change of co-factors in acidic, base or hydrolytic reactions or in the aqueous media. The process should be regiospecific, rapid and without additional steps to add time and cost and provide for easy separation of products from the enzyme system.

As seen from the above, meeting the requirements for NAD(P)$^+$/NAD(P)H replacement is not easy, particularly when large scale oxido-reduction processes are contemplated.

III. Novel biomimics for replacement of NAD(P)$^+$/NAD(P)H system

With understanding of the requirements for successful replacement or regeneration of NAD(P)$^+$/NAD(P)H co-factors as described above, several groups of compounds were investigated as possible candidates for such NAD(P)$^+$/NAD(P)H co-factors replacement or regeneration. The particular emphases was placed on their being water soluble or swellable as the enzymatic reactions proceed optimally in an aqueous milieu. However, for large scale, high volume industrial enzymatic oxido-reductive reactions, the acqueous/organic medium is not only permissible but often preferred for cost effectivity.

First group of compounds which was studied as possible regeneration or replacement co-factors comprised a family of pyridinium compounds, particularly variously substituted 1-benzylnicotinamides, using simple organorhodium complexes as catalyst for their reduction. These organorhodium complexes can regiospecifically transfer hydride ion, either chemically or electrochemically generated, to these pyridinium compounds to exclusively provide reduced forms of 1-benzylpyridinium salt. This group of biomimics was found to be not very water soluble but performed well in water/organic solvent medium.

The second group of compounds which was investigated included a group of compounds comprising ribose and phosphate groups with structural characteristics more aligned with the natural NAD(P)$^+$, and its reduced 1,4-dihydro derivative 1,4-NAD(P)H. These compounds are represented by β-nicotinamide-ribose-5'-methyl phosphate (6) but also include compounds comprising other alkylation groups, ethyleneglycol chains, or other polymer groups replacing the methyl group, added for the purpose of separation or immobilization. These compounds are readily water soluble and meet many of the requirements for successful replacement of NAD(P)$^+$/NAD(P)H system, as listed above, and additionally permit manufacture of biosensors or other devices of the invention.

Model biomimetics whether soluble in water/organic solvent mixture or solely water soluble are intended to be within the scope of the invention. The representative compounds were prepared and tested according to Examples 1–11.

A. Biomimics for oxido-reductive enzymatic reaction

Novel biomimetic compounds of the invention are generally depicted by the formulae I and II

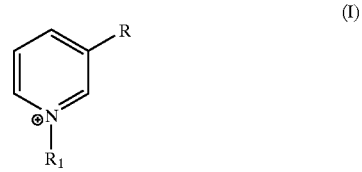
(I)

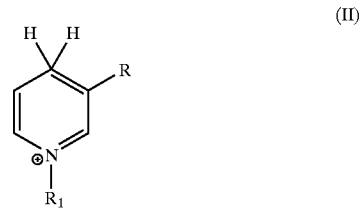
(II)

wherein is —CN, —C(O)NH$_2$, —C(O)NHCH$_3$, —C(S)NH$_2$, —C(O)CH$_3$, or —C(O)OCH$_3$;

wherein R$_1$ is —(CH$_2$(CH$_2$O)$_n$YR$_2$, ribose-Y—R$_2$, or

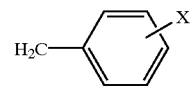

wherein Y is —OPOO—, —OBO$_2$—, —OSO$_2$—, CH$_3$NH—, —(CH$_2$)$_n$NH—, adenine, or imidazole;

R$_2$ is H, CH$_3$, —(OCH$_2$CH$_2$)$_n$, —(NCH$_2$CH$_2$)$_n$— or —[(N═P(OCH$_3$)$_2$]$_n$;

wherein X is —OCH$_3$, —CF$_3$, —O(CH$_2$CH$_2$O)$_n$ or —OPOOR$_2$;

wherein R$_3$ is H, —CH$_3$, —(OCH$_2$CH$_2$)$_n$, —(NCH$_2$CH$_2$)$_n$— or —[N═P(OCH$_3$)$_2$]$_n$;

wherein n is 1–2000; or a salt thereof.

Y may be phosphate or another ionic group such as borate or sulfate that may act to buffer the solution by providing a source of protons. Similarly, bases such as adenine, imidazole or alkyl amines might be incorporated as Y to provide basic buffering.

The polyethylene oxide chains may be replaced by other chains such as polyamines or polyphosphazenes depending on their solubility or swellability in the solvent used. The length of the chains will depend on whether the chains are tethered to a solid support such as an insoluble polymer network, silica particles and the like or whether the molecule should be soluble in the solution. For the insoluble support the chain lengths need only be long enough to ensure that the nicotinamide moiety can penetrate to the enzyme center. For soluble systems the length needs to be long enough to ensure that the co-factors do not penetrate a size selective membrane, thereby ensuring that no losses of the valuable co-factor mimic occurs during product separation and co-factor recovery.

The solid support system is shown in the below diagram.

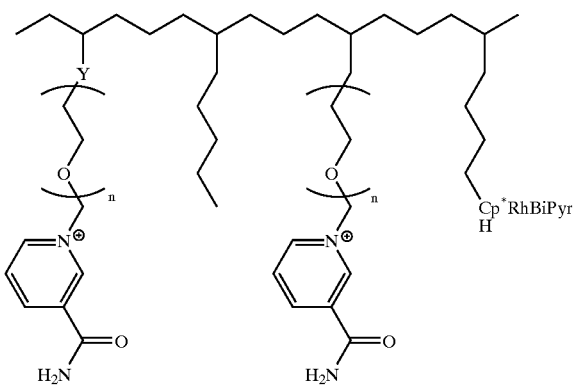

The diagram shows incorporation of Y-substituent in the polymeric chain and the incorporation of the rhodium catalyst and an anion, such as triflic acid.

The diagram shows how the biomimetic co-factors may be incorporated into a polymer membrane by co-polymerization of the nicotinamides that are N-substituted with polymerizable groups. The polymer chains containing groups Y provide buffering capacity. The monomers thus described may be co-polymerized with monomers that contain acid groups such as, for example, $CF_2SO_8H$ or the rhodium pre-catalyst. Such polymers form swellable matrices that provide species to accommodate the acid-base and redox chemistry required for the redox system. The polymer membrane or immobilized material facilitates separation of the co-factor regeneration system from the reaction substrates and products and prevents loss of the active regeneration species.

B. 1-Benzylnicotinamide triflate-type biomimetics

In the first stage of development of this invention, the investigated compounds were 1-benzylpyridines of 1-benzylnicotinamide-type.

Initially, the studies were directed to regiospecificity of 1-benzylnicotinamide compounds. These studies, partially described in Angew. Chem. Int. Ed., 38(10):1429 (1999), utilized the $NAD^+$ biomimetic compound 1-benzylnicotinamide triflate for regeneration of $NAD^+$/NADH system. This compound, also known as 1-benzylpyridinium triflate, was reduced to its reduced derivative 1,4 dihydro-1-benzylnicotinamide triflate by using the rhodium catalyst precursor $[Cp^*Rh(bpy)(H_2O)]$ $(OTf)_2$ and sodium formate as the hydride source. The reduction was found to be highly regiospecific. Subsequently, a variety of 3-substituted derivatives of 1-benzylnicotinamide triflate were synthesized according to Example 2 and studies were performed to determine how other R-substituents in position 3 influence the regioselectivity. Results are illustrated in FIG. 1.

Figure 1B:
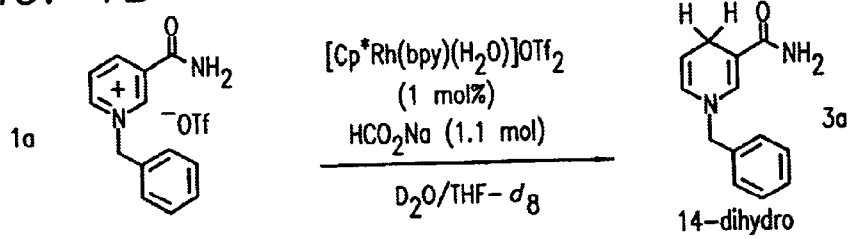
FIG. 1B illustrates regioselective reduction of the 1-benzylnicotinamide (1a) wherein R is —$CONH_2$ using sodium formate as hydride source and [Cp*Rh(bpy)(H$_2$O)](OTf)$_2$ as a catalyst precursor into its 1,4-dihydronicotinamide (3a).
Figure 1C:
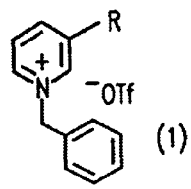
FIG. 1C lists R substituents and shows relative rates and turnover frequencies of the regioselective reductions of 1-benzylpyridinium derivatives 1a–1i depicted in FIG. 1A.

FIG. 1A illustrates synthesis of variously substituted 1-benzylpyridinium derivatives comprising biomimics (1a–1i) depicted as compounds (1a)–(1i) in FIG. 1C, wherein compound (1a) corresponds to 1-benzylnicotinamide triflate. The 1-benzylnicotinamide compounds were synthesized from appropriately 3-substituted pyridinium reacted with benzylchloride in tetrahydrofurane solvent in the presence of sodium triflate. Pyridinium was substituted on the 3-position with R-substituents (a)–(i), as seen in FIG. 1A. Resulting 3-substituted derivatives of 1-benzylpyridinium triflate, compounds (1a)–(1i), were then submitted to regiospecific reduction as shown in FIG. 1B illustrating the reduction of compound (1a) to its reduced derivative 1,4-dihydronicotinamide (3a).

FIG. 1B shows regioselective reductions of the $NAD^+$ model, 1-benzylnicotinamide triflate (1a), by using sodium formate as hydride source and rhodium $[Cp^*Rh(bpy)(H_2O)]$ $(OTf)_2$, compound (2), as a catalyst precursor. $^1H$ NMR spectroscopy in 1:1 $D_2O$/THF-$d_8$ with compound (1) and the catalyst precursor (2) in the presence of the hydride source ($HCO_2Na$), showed formation of the reduced 1-benzyl-1,4-dihydronicotinamide, compound (3a) as a predominant isomer.

Because some of the compounds (1a)–(1i) were found to be only partially water soluble, the studies were performed in a mixture of tetrahydrofuran and water. Such partial water solubility may affect their utility as effective $NAD(P)^+$/$NAD(P)H$ regeneration agents in oxido-reduction reactions in physiological conditions. However, such limited water solubility may provide advantage for their industrial use in high volume, large scale oxido-reductive processes.

Comparative relative rates and turnover frequencies of each 3-substituted 1-benzylnicotinamide are shown in FIG. 1C. The relative rates, seen tabulated in FIG. 1C, were determined by observing disappearance of the pyridinium signals versus an internal standard, $[(CH_3)_4N]OTf$ (tetramethylammonium triflate), during the first 2 hours, where the relative rate of 1-benzylnicotinamide triflate (1) was set to 1.0. The turnover frequencies were calculated by the formation of mmol of product/mmol of catalyst/hour. The total turnover number in 24 hours was ~95 for all substrates that gave product. The reactions were conducted in presilylated J. Young NMR tubes and were followed by $^1H$ NMR.

As seen in FIG. 1C, relative rates of signals disappearance for compounds (1b)–(1i) were in the 0.9 to 1.3 range compared to compound (1) 1-benzylpyridinium triflate, set to 1.0. Additionally, when the 3-substituent presented a steric effect, such as in compound (1c), where the R-substituent is $C(O)NH(CH_2CH_3)_2$, or when the R-substituent has a non-binding group, such as —$CH_3$ in compound (1h) or —H in compound (1i), the catalytic hydride transfer was not observed even with the 2 and 6 ring positions being readily available for such transfer and more electrophilic. These later findings indicate the crucial coordination of the biomimic to the $CP^*Rh$ metal ion center.

The above described results show that the reduction of the $NAD^+$biomimic compound (1), namely 1-benzylnicotinamide triflate into 1,4-dihydrobenzylnicotinamide performed under the above described conditions, results in almost exclusive 1,4-NADH regiospecificity wherein the 1-benzyl substituent on the nitrogen atom was shown to exert a substantial electron-withdrawing effect on the hydride transfer and increased the rate of conversion two times in comparison with the methyl derivative. The kinetics of the conversion was affected by the concentrations of the catalyst precursor $[Cp^*Rh(bpy)(H_2O)]^2$, the substrate 1-benzylnicotinamide triflate and the hydride source $HCO_3Na$ in THF/water (1:1) medium. In water, the concentration of the biomimic did not effect the rate.

The biomimic compounds, described above, were only moderately water soluble and organic solvent needed to be added to observe reductive reactions. For effective $NAD(P)^+$/$NAD(P)H$ replacement, as already discussed above, compounds which are water soluble are preferred, although for industrial enzymatic oxido-reduction reactions in a water/solvent mixture often increases efficiency and decreases cost.

C. Water soluble β-nicotinamide ribose-5'-methyl phosphate-type biomimics

The ultimate goal of the invention was to prepare water soluble/swellable biomimics having regiospecific, stereospecific and chemospecific properties equivalent to NAD+ co-factor.

The first aqueous biomimics were designed to be structurally similar to NAD+, comprising both the ribose and phosphate groups as well as lower alkyls from 1 to 6 carbons and/or polymers based on polyethylene glycol. The exemplary compound β-nicotinamide ribose-5'methyl phosphate (6) was synthesized from a commercially available precursor, β-nicotinamide ribose-5'-phosphate, compound (5), via a methylation reaction using dicyclohexylcarbodiimide (DCC) and a catalytic amount of dimethylaminopyridine (DMAP) in methanol. The preparation method for compound (6) is described in Example 4.

The structure of β-nicotinamide ribose-5'methyl phosphate and its synthesis from β-nicotinamide ribose-5'-phosphate, compound (5) are shown in FIG. 2A. FIG. 2B illustrates regioselective reduction of β-nicotinamide ribose-5'methyl phosphate (6) into its reduced derivative 1,4-dihydro-β-nicotinamide-ribose-5'methyl phosphate (7). The turnover frequency (TOF) in the regioselective reduction of compound (6) to compound (7) was 20 hour$^{-1}$, that is approximately 2.5 times higher turnover frequency than those of compounds (1a)–(1i). Compared to the TOF of the natural NAD+, which under the same conditions was determined to be 18 hour$^{-1}$, the TOF of the above water soluble co-factors was the same or slightly higher and in any case comparable to the natural NAD+. The 1,4-dihydro analog (7) and the compound (6) were found to be completely water soluble.

The novel compound (6) has shown activity in enzymatic systems and have been shown to be recognized by horse liver alcohol dehydroglucose HLADH for catalyzed, highly enantio-selective synthesis of organic compounds, such as synthesis of chiral alcohols from achiral ketones. Moreover, as will be described below in greater detail, HLADH recognition of biomimics in their reduced form does not depend on the presence of the ribose, pyrophosphate or adenosine functionalities to provide chiral products. These studies thus prove that only the pyridinium comprising portion, such as nicotinamide portion, of the molecule is truly necessary for stereoselective reduction of the substrate to the product.

Consequently, the biomimics of the invention are compounds which contain variously substituted pyridinium, such as, for example, nicotinamide, typically further substituted at the 1-position.

A second generation of biomimic co-factors, seen in FIG. 3, was prepared subsequently. These biomimics are aqueous nicotinamides which may be easily incorporated into polymeric matrices to provide devices for replacement of the NAD(P)$^+$/NAD(P)H system. As seen in FIG. 3, nicotinamide compound (8) when reacted with compound (9), wherein n is 1–500, for example as seen here 1-(8-hydroxy-3,6-dioxaoctanyl)-3-carbamoyl-pyridinium bromide wherein n=2, results in formation of biomimic compound (10), namely 1-(8-acryloyloxy-3,6-dioxaoctanoyl)-3-carbamoylpyridinium bromide. This compound is both water and organic solvent soluble for both oxidized and reduced forms. Compound (10) may be easily incorporated in polymeric membranes or solid polymer support systems seen as compound (11) in FIG. 3.

FIG. 3 illustrates a method of substituting the nicotinamide compound (8) in 1-position with a polymer (9) to yield a biomimic with a polymer tether, seen as compound 10. Compound 10 is then functionalized to yield an arylic compound (11) which may be used to undergo polymerization to yield a polymer matrix such as that shown in FIG. 4.

The polymer support may be polyethyleneglycol, polyvinylglycol, polystyrene, polyalkylamine, polyphosphosene or polyethylene of various lengths, and M. W. up to 200,000 such as, for example, PEG 200, PEG 400 or PEG 600. The length of the polymer chain can be short or very long depending upon the configuration of the device. The polymerizable compound (10) may be incorporated in a polymer membrane as shown in FIG. 3. Polymer support may take the form of a membrane on an electrode, a solid polymer mass or an easily recoverable polymer as seen in FIG. 4.

Figure 4:
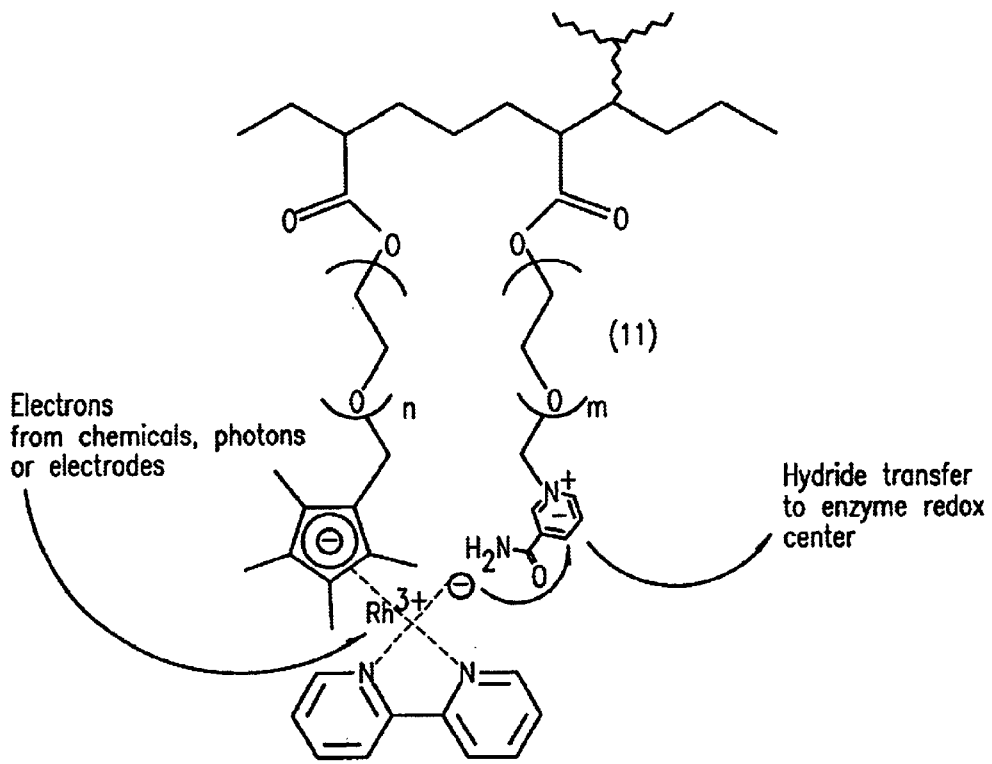
FIG. 4 illustrates utility of novel biomimics for regeneration of NAD(P)+/NAD(P)H system when incorporated into polymer support of a biosensor or chemical membrane device.

FIG. 4 shows biomimic compound (11) copolymerized with an acrylate ether monomer containing the rhodium catalyst. This polymer matrix is suitable for use with reducing agents, chemicals, photons or electrodes to yield the enzymatically active co-factor in a fashion that allows easy separation of the regeneration system from the products of the enzymatic reaction. FIG. 4 also illustrates transfer of electrons from chemicals, photons or electrodes as well as hydride transfer to rhodium containing enzyme redox center.

The system described in FIG. 4 is able to replace the NAD(P)$^+$/NAD(P)H system with the correct regiospecificity and also possesses other advantages. The biomimic or the polymer comprising system does not contain the sugar or phosphate group that can undergo acid/base reactions that could inactivate the co-factor. The polymer matrix, such as PEG groups, provide a means to tether or recover the co-factors and the expensive rhodium compound acting as a catalyst precursor.

The much less expensive nicotinamide biomimic compound thus provides the system that is much less expensive than NAD(P)$^+$/NAD(P)H system even if fewer regeneration cycles are carried out before replacement is needed. The system can be used for much higher volume processes with a lower product price.

The polymer tethers can be tailored to provide close control of the reaction conditions by these means in addition to providing means to recover the expensive reagents and separate the products from the enzyme and the other reactants.

D. Catalyst precursors

Regiospecific reductions according to the invention are catalyzed by compounds which permit or assist in regiospecific rearrangement during the reduction reaction. These compounds, herein called catalysts precursors (2), are preferably a metal hydride complexes comprising rhodium, iridium, nickel, ruthenium, cobalt or zinc. The most preferred complex comprises rhodium compound [Cp*Rh(bpy)(H$_2$O)] triflate. Catalyst precursor is thus a compound which is reduced by a reducing agent (20) to form the hydride catalyst (22) for the reduction of the co-factor.

One catalyst precursor suitable for catalyzing regiospecific reductions is [Cp*Rh(bpy)(H$_2$O)](OTf)$_2$. In the alternative, the catalyst precursor may be prepared with other suitable anions such as tetrafluoroborate, phosphate, sulfate, nitrate, perchlorate and such others.

The catalyst precursor [Cp*Rh(bpy)(H$_2$O)](OTf)$_2$ (as a triflate salt) was prepared by the reaction of [Cp*Rh(H$_2$O)$_3$](OTf)$_2$ with 2,2'-bipyridine conducted in water according to Example 5. The reaction provides [Cp*Rh(bpy)(H$_2$O)](OTf)$_2$, compound (2), in 77% isolated yield. Since the triflate salt complex had not been previously reported, the structure of the catalyst precursor (2) was determined by crystallographic X-ray analysis.

Table 1 shows crystallographic information.

TABLE 1

| Crystallographic Data for Rhodium Complex (2) | |
|---|---|
| Compound | [Cp*Rh (bpy) (H$_2$O)] (OTf)$_2$ |
| Empirical Formula | C$_{22.3}$H$_{27}$F$_6$N$_2$O$_{7.7}$RhS$_2$ |
| Formula Weight | 728.29 |
| Crystal size | 0.40 × 0.36 × 0.16 mm |
| Crystal habit | Parallelepiped |
| Crystal color | Yellow |
| Crystal system | monoclinic |
| Space group | P2$_1$/C |
| Unit Cell Dimensions | a = 12.411 (3) Å α = 90° |
| | b = 15.811 (3) Å β = 97.44 (3)° |
| | c = 14.258 (3) Å γ = 90° |
| Volume | 2774.3 (10) Å$^3$ |
| Z | 4 |
| Density (calculated) | 1,741 mg/cm$^3$ |
| Absorption coefficient | 0.854 mm$^{-1}$ |
| F (000) | 1470 |
| Max. and min. transmission | 0.898 and 0.757 |

Table 2 shows selected bond lengths and angles for the typical piano stool structure of compound (2).

TABLE 2

| Data Collection for [Cp*Rh (0.7H$_2$O/0.3CH$_3$OH)bpy] (OTf)$_2$ · 0.7H$_2$O | |
|---|---|
| Diffractometer | Siemens R3m/v |
| Temperature | 130 (2) K |
| Radiation Source | normal-focus sealed tube |
| Wavelength | 0.71073 Å (MoKα) |
| Monochromator | graphite |
| θ range for data collection | 1.65 to 27.50° |
| Scan type | ω |
| Index ranges | −3 ≤ h ≤ 17, −3 ≤ k ≤ 20, −18 ≤ l ≤ 18 |
| Reflections collected | 8986 |
| Independent reflections | 6371 (R$_{int}$ = 0.0520) |
| Standard reflections | 2 |
| % decay of standards | <0.1 |

Similarly to the rhodium catalyst precursors, other metal ions such as zinc, nickel, cobalt, ruthenium or iridium, for example, may be advantageously utilized as catalysts for the reduction of the current biomimic compounds to their reduction derivatives.

E. Reducing agent

A reducing agent used in this reaction reduces precatalyst to catalyst under conditions compatible with the enzymes. Examples of reducing agents are formate, hydrogen, sodium borolydride, hydroguinone, sodium, thiosulfate, electrodes and photons.

F. Regeneration of biomimics

In order to have utility as an NAD(P)$^+$/NAD(P)H system replacement, the biomimic compounds of the invention themselves must be able to be regenerated. The regeneration system coupled with enzyme synthesis is illustrated in FIG. 5.

Figure 5:
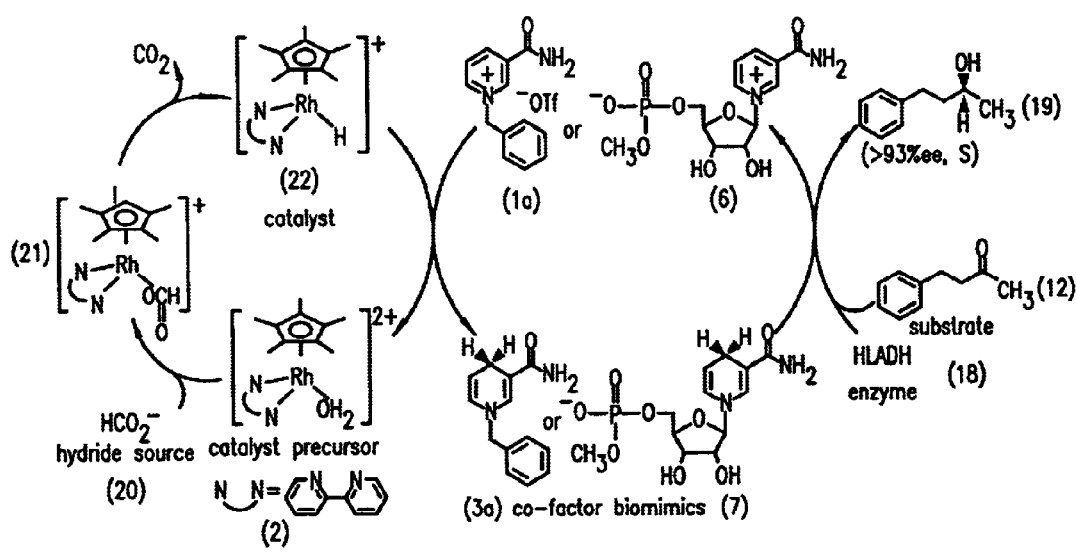
FIG. 5 is a scheme illustrating catalytic cycle for the regioselective reduction of the biomimic compounds (1) and (6) with rhodium containing catalyst precursor (2), reducing agent (20) and a catalyst (22) to yield the enzymatically active compounds (3a) and (7) that provide the hydrogen for the HLADH enzymatic reduction of the ketone (12) into the enantiomerically pure alcohol (19).

FIG. 5 shows chiral synthesis experiments with biomimics (1) and (6) illustrating the oxido-reduction effect of both biomimics on the conversion of achiral ketone benzylmethyl ketone (12) to corresponding alcohol (19). In the process of such chiral conversion in the presence of horse liver alcohol dehydrogenase (HLADH), both biomimics (1) and (6) gave similar chiral synthesis results as seen in FIG. 5. Both biomimics yielded >93% ee(S-enantiomer)and both had similar turnover frequencies of about ~30 d$^{-1}$. These results were similar to results obtained previously with NAD$^+$ as a control experiment.

The results described above not only confirm that both groups of the above described biomimics are suitable for replacement of NAD(P)$^+$/NAD(P)H system in the oxidoreduction reaction, but also confirm that all that is needed for such a function is nicotinamide portion of the molecule as long as it is able to be reduced to its 1,4 dihydroderivative.

As seen in FIG. 5, the reduction of the biomimic (1) or (6) involves hydrid transfer elicited from reaction of the rhodium catalyst precursor (2) in the presence of the reducing agent (20), namely hydrid source HCO$^-$$_2$, to form a metal hydrid [Cp*Rh(bpy)H]$^+$ (21) and the catalyst (22) which affects the binding of the biomimic (1a) or (6) with the catalyst (22) leading to reduction of the biomimic (1) or (6) into their corresponding reduced derivatives (3) or (7). When alcohol (19) is oxidized to ketone (12) the oxidized compounds (1) and (6) are reduced to their reduced forms (3) and (7). When the ketone (12) is reduced to alcohol (19) by HLADH (18), the opposite reaction ensues, namely, reduced compounds (3) and (7) are converted into their nonreduced forms.

FIG. 5 thus illustrates the cyclic and ongoing process for oxido-reduction reactions of either oxidases (not shown in FIG. 5) or reductases, such as HLADH, shown in FIG. 5. Oxidation reaction, logically, is catalyzed in the same way as is reduction, except that the oxidation reaction proceeds in the opposite direction and thus accompanies the reduction of the biomimic into its oxidized product.

G. Regioselective reduction of biomimics with organorhodium complexes

The novel biomimics of the invention were extensively tested in the following studies.

1. Competitive reaioselective reduction reactions

The first study compared the σ-donating ability and the electron-withdrawing substituent effect.

In order to establish whether the σ-donating ability or the electron-withdrawing effect of the 3-substituent of the 1-benzylnicotinamide was the important parameter, several competitive substrate reduction experiments were performed.

For this purpose, the compound (1a) 1-benzylnicotinamide, was reduced with rhodium catalyst precursor (2) in the presence of its alternatively substituted derivatives, compounds (1e), substituted with —C(O)—CH$_3$, (1g), substituted with (—CN), (1d), substituted with —C(S)NH$_2$ or (1f), substituted with —C(O)OCH$_3$, and their competitive reduction was determined.

When the compound (1a) 1-benzylnicotinamide was reduced in the presence of either compound (1e), having a competitive rate =0.9, or the compound (1g), having a competitive rate =0.8, the compound (1a) substituted with a —C(O)NH$_2$ group was found to be more reactive that either the —C(O)CH$_3$ or —CN analogs (1.1 and 1.3 times faster, respectively). When the compound (1) was reduced in the presence of compound (1d) or compound (1f), both the —C(S)NH$_2$ and —C(O)OCH$_3$ derivatives were found to be more reactive (1.3 and 1.2 times faster, respectively).

Thus, the σ-donating ability of the 3-substituent (e.g., compounds (1a), (1d) and (1f)) is more important parameter in binding to Cp*Rh, than the incipient electron-withdrawing effect of this group (e.g. compounds (1e) and (1g)) in the overall reduction reaction.

These findings show that the majority of these compounds are able to transfer hydride to 1,4 position and hence are active co-factors in enzymatic oxido-reductive reactions.

2. The effect of 1-substituted nicotinamide substrates on the relative rate/turnover frequency of the regioselective reduction The electronic effect of different substituents bound to the nitrogen atom of the nicotinamide nucleus was also examined.

The electronic effect of differently substituted nicotinamide substrates was determined by their relative rates. The relative rates of these compounds were determined by observing the disappearance of the pyridinium signals compared to interval standard, [(CH$_3$)$_4$N]OTf, during the first 2 hours, where the relative rate of compound (1a) was 1.0.

For this purpose, the 1-benzyl group in compound (1a) was replaced with a 1-methyl group, to provide 1-methylnicotinamide according to Example 3.

Results obtained with these studies indicated that this change in substituent reduced the relative rate to 0.5, providing a relative rate ratio of 1-benzyl/1-methylnicotinamide of 2.0. The 1-benzyl group was thus found to be a better electron-withdrawing substituent in comparison to the electron-donating 1-methyl group. This facilitated hydride attack at 4-position. Plausible electron reorganization upon hydride transfer to 4-position thus benefits from a through bond electron-withdrawing substituent on the nitrogen atom of the nicotinamide nucleus.

When the β-nicotinamide ribose-5-methyl phosphate in water was compared with 1-benzylnicotinamide in THF/water, its turnover frequency (TOF) was found to be about 2.5 times higher than those of 1-benzylnicotinamide.

These findings show that the nature of the N-substituent (position 1) on pyridinium and the solvent used affects the rates of hydride transfer and hence, affects the enzymatic activity.

3. Kinetic and activation parameters for the regioselective reduction of biomimic compounds (1) and (6) with rhodium catalyst precursor The kinetics of the regioselective reduction reactions were further studied utilizing UV-vis techniques with the two biomimic compounds (1) and (6) and the results were compared to NAD$^+$ itself. Experimental conditions are described in Example 9.

The effect of the initial rate ($r_i$) at low conversions to the 1,4-dihydro product (~10%) was ascertained by varying the amount of substrate precatalyst (2) and sodium formate concentrations. Table 3 shows the effect of changing the concentration of compound (1) the initial rate of regioselective reduction.

The initial rates ($r_i$) of formation of compound (3) were obtained from plots of concentration (absorbance at 354 nm/ε) versus time at low conversions (~10%). The values of $k_{cat}$ were calculated at 299° K.

Table 3 shows initial rates ($r_1$) and $k_{cat}$ of regioselective reductions of different concentrations of 1-benzylnicotinamide (1) at 299° K in 1:1 H$_2$O/THF.

The initial rates $r_i$, seen in Table 3 of the regioselective reductions were found to be concentration dependent for compounds (1), (6) or NAD$^+$, and also for the catalyst precursor [Cp*Rh(bpy)H]$^+$, at steady state concentrations of the hydride source, sodium formate, with precatalyst (2).

A comparison of the initial rates and turnover frequencies of regioselective reduction for the two models, compounds (1) performed in acqueous/organic solvent medium and (6) with NAD$^+$ (H$_2$O) performed in acqueous conditions at 294° K is shown in Table 4.

TABLE 4

Comparison of Initial Rates ($r_i$) and TOF for 1-Benzylnicotinamide, β-Nicotinamide Ribose-5' Phosphate, and NAD$^+$ at 294° K.

|  | NAD$^+$ | Compound (6) | Compound (1a) |
|---|---|---|---|
| Substrate$^a$ (M) | $1.55 \times 10^{-3}$ | $1.55 \times 10^{-3}$ | $4.29 \times 10^{-3}$ |
| HCO$_2$Na (M) | $2.03 \times 10^{-2}$ | $1.92 \times 10^{-2}$ | $5.39 \times 10^{-2}$ |
| Compound 2 (M) | $1.58 \times 10^{-5}$ | $1.49 \times 10^{-5}$ | $4.33 \times 10^{-5}$ |
| $r_i$ (M s$^{-1}$) | $3.10 \times 10^{-8}$ | $2.82 \times 10^{-8}$ | $1.23 \times 10^{-8}$ |
| TOF (h$^{-1}$)$^b$ | 9 | 7 | 2 |

$^a$Compound (6), β-nicotinamide ribose-5-methyl phosphate and NAD$^+$ in H$_2$O at pH 6.54; Compound (1a), 1-benzylnicotinamide in 1:1 H$_2$O/THF; Compound (2), rhodium catalyst precursor;
$^b$mmol [1,4-dihydrol]/mol of [Cp*Rh (bpy)H]$^+$.

Rates were obtained via UV-vis techniques and are an average of two runs.

As seen from Table 4, initial rate of regioselective reduction of the aqueous biomimic compound (6) are clearly comparable to NAD$^+$. Both compound (6) and NAD$^+$ in acqueous medium have initial rates that are ~3 times higher than compound (1) in THF/H$_2$O; (1:1) at comparable concentrations. Significant increases in TOF and values of $k_{cat}$ were also observed.

The effect of the solvent, that is, water or the organic solvent THF, on the rate of formation of the reduced forms of biomimics 1-benzyl-1,4-dihydropyridine, 1,4-dihydronicotinamide ribose-5'methyl phosphate and NADH (3) was also studied. The initial rate enhancement observed in acqueous conditions for compound (6) and NAD$^+$ (Table 4) were compared to initial rates of compound (1a) reduction

TABLE 3

Regioselective Reductions at Difference Concentrations of 1-Benzylnicotinamide (1a)

| Compound [1a] (M) | $2.68 \times 10^{-3}$ | $1.61 \times 10^{-3}$ | $1.07 \times 10^{-3}$ | $5.37 \times 10^{-4}$ | $2.68 \times 10^{-4}$ |
|---|---|---|---|---|---|
| [HCO$_2$Na] (M) | 0.03266 | 0.03260 | 0.03266 | 0.03259 | 0.03266 |
| Compound [2] (M) | $2.725 \times 10^{-5}$ | $2.725 \times 10^{-5}$ | $2.725 \times 10^{-5}$ | $2.725 \times 10^{-5}$ | $2.725 \times 10^{-5}$ |
| $r_1$ (M s$^{-1}$) | $3.43 \times 10^{-8}$ | $2.01 \times 10^{-8}$ | $1.20 \times 10^{-8}$ | $6.30 \times 10^{-9}$ | $2.1 \times 10^{-9}$ |
| $k_{cat}$ (M$^{-2}$s$^{-1}$) | 14.38 | 14.03 | 12.61 | 13.02 | 8.85 |

Compound [1a] is 1-benzylnicotinamide;
Compound [2] is rhodium catalyst precursor;
HCO$_2$ is the hydride source sodium formate;
$r_1$ is initial rate;
$k_{cat}$ is rate constant for catalysis.

performed in THF/H$_2$O in ratio from 1:1 to 1:4. Decreased ratio of the organic to acqueous solvent caused increase in the initial rate of formation of the 1,4-dihydro derivative (3a)—by a factor larger than 6, at comparable concentrations.

Results are seen in Table 5 where the TOFs for 1-benzylnicotinamide were determined at different ratio of THF to water, namely 1:1 and 4:1; water/THF at different concentrations of the biomimic (1a).

TABLE 5

Initial Rate of the Regioselective Reduction of 1-Benzylnicotinamide Triflate at Different Ratios of $H_2O$/THF and Concentrations

| | | | |
|---|---|---|---|
| Compound 1a (M) | $4.29 \times 10^{-3}$ | $4.82 \times 10^{-3}$ | $1.68 \times 10^{-3}$ |
| $HCO_2Na$ (M) | $5.39 \times 10^{-2}$ | $5.52 \times 10^{-2}$ | $1.79 \times 10^{-3}$ |
| Compound 2 (M) | $4.33 \times 10^{-5}$ | $4.83 \times 10^{-5}$ | $1.71 \times 10^{-5}$ |
| $H_2O$/THF | 1:1 | 4:1 | 4:1 |
| THF (M) | 10.10 | 4.042 | 4.042 |
| $r_i$ (M s$^{-1}$) | $1.23 \times 10^{-8}$ | $1.75 \times 10^{-7}$ | $4.31 \times 10^{-8}$ |
| TOF (h$^{-1}$) | 2 | 13 | 10 |

1 = 1-benzylnicotinamide triflate
2 = rhodium catalyst precursor

As seen in Table 5, both the concentration of the biomimic substrate (1a) and the ratio of water to organic solvent affected both the initial ratio of conversion and turnover frequency.

The decrease in initial rate of regioselective reduction shown in Table 5 confirms the importance of the acqueous biomimics. The observed results suggest that THF decreased the binding of compound (1a) with the presence of the catalyst precursor [Cp*Rh(bpy)H]$^+$ metal ion center and affects the equilibrium for substrate-catalyst binding, the presumed rate determining step. Also noticeable is an increase of the initial rates of compound (1a) in 4:1 $H_2O$/THF, seen in Table 5, column 3. These rates are now comparable to values obtained with compound (6) and with NAD$^+$ in water, seen in Table 4, columns 1 and 2.

The results of these kinetic studies show that the simple biomimic compounds transfer hydride as rapidly as more complicated and expensive ribose containing biomimics and NAD$^+$. Complex ribose, sugar, phosphate and adenine are not necessary for such transfer.

H. Regioselectivity of biomimics of the invention

As described above, biomimic compound 1-benzylnicotinamide triflate (1a) can be converted exclusively into its reduced form 1-benzyl-1,4-dihydronicotinamide (3a) when reacted with [Cp*Rh(bpy)($H_2O$)](OTf)$_2$, (2), as the catalyst precursor, in the presence of sodium formate (20) as the hydride source. Reaction is shown in FIG. 1B.

In addition, an aqueous NAD$^+$ model, β-nicotinamide-5'-ribose methyl phosphate (6), seen in FIG. 2A, demonstrated similar regioselective reduction with in situ formed [Cp*Rh(bpy)H]$^+$ to the corresponding 1,4-dihydronicotinamide-5'-ribose methyl phosphate (7).

The biomimic compound (6) possesses some structural similarities to NAD$^+$, with particular emphasis on the mono-ribose phosphate moiety, but contains no pyrophosphate nor adenosine substituents. The structure of the biomimic compound (1a) has a simple 1-benzyl group in place of the ribose, pyrophosphate, and adenosine groups.

The high regiospecificity for the biomimics of the invention seems to be due to the binding of the carbonyl of the 3-substituent group of the biomimic to a ring-slipped η$^3$-Cp*Rh metal ion center (opening a coordination site) that provides a constricted six-member ring transition state/intermediate for regiospecific hydride transfer to C4 position of the nicotinamide.

Comparative studies performed and described herein evidence that such structural similarities are not necessary for regioselectivity and proper function as the NAD$^+$ replacement as long as the nicotinamide or pyridinium portion of the compound is present.

IV. Chiral synthesis of alcohols and enzymatic reductions of ketones

Practical use of the invention was tested on chiral synthesis of alcohols. The initial rates ($r_i$) of the regioselective reduction of both compounds (1a) in THF/$H_2O$ (1:4) and (6) in $H_2O$ at pH 6.54 with in situ generated [Cp*Rh(bpy)H]$^+$ to their corresponding 1,4-dihydro analogs were very comparable to NAD$^+$ itself. Therefore, use of both compounds (1) and (6) as biomimics of NAD$^+$ in chiral reduction reactions was attempted in conjunction with the above-mentioned co-factor regeneration method, with the stipulation that the enzyme which was to be utilized, horse liver alcohol dehydrogenase (HLADH), should be able to recognize the simplified reduced forms, that is the reduced compounds (3) and (7).

Previously, an X-ray structure of the NAD$^+$ binding site in the HLADH enzyme was found to show that the adenosine stabilized this interaction by being in a hydrophobic area of the enzyme, while the faces of the nicotinamide group were both in a hydrophilic and hydrophobic site. The role of each substituent on the 1,4-dihydronicotinamide nucleus, including ribose, pyrophosphate and adenosine groups of the current biomimics was then investigated for enzymatic molecular recognition and chiral reduction with most important structural feature still present in the new biomimic comprising the 1,4-dihydronicotinamide nucleus.

Figure 6:
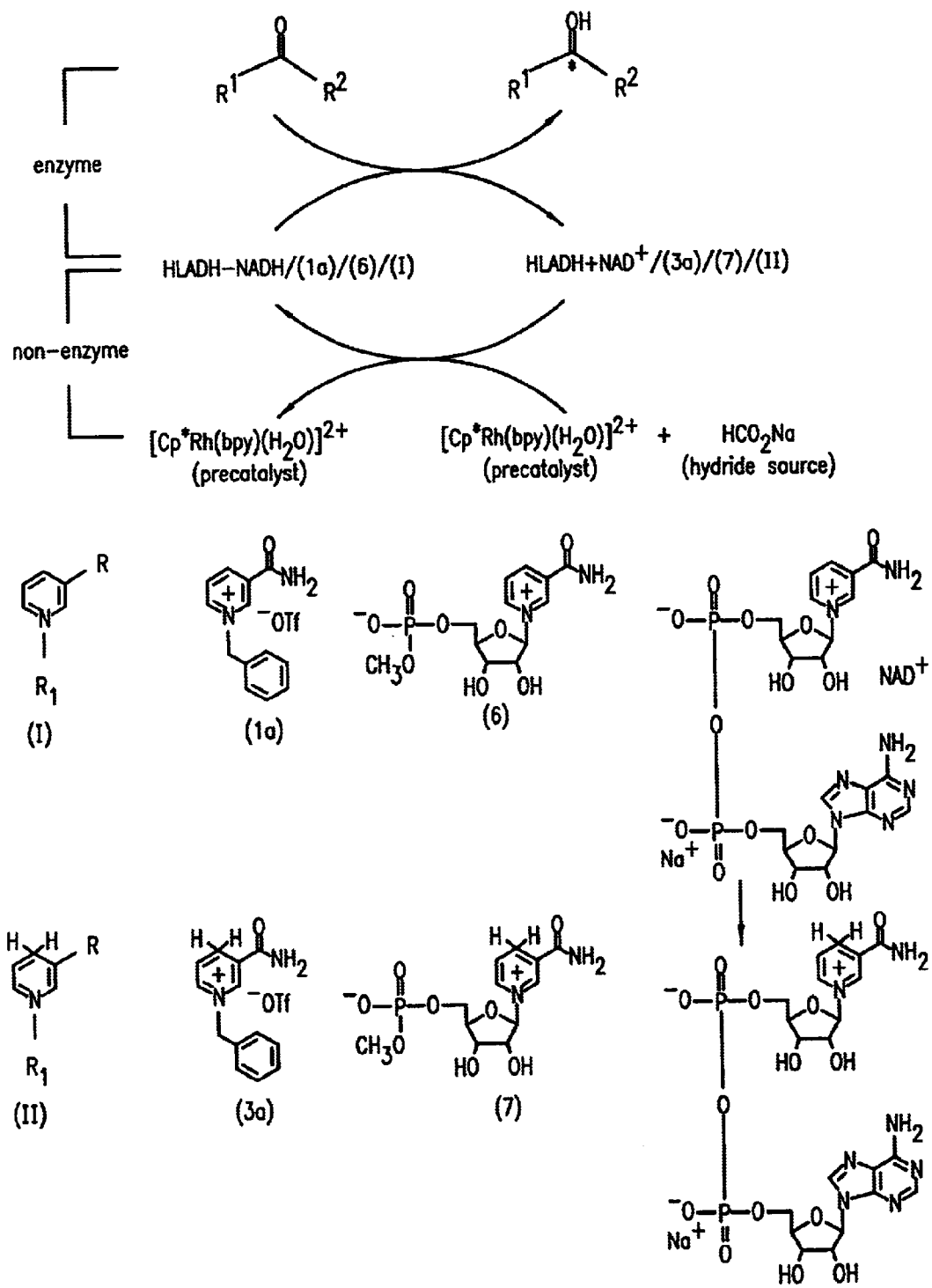
FIG. 6 illustrates enzymatic reduction of achiral ketones to alcohols using biomimics of the invention as co-factors for horse liver alcohol dehydrogenase (HLADH).

Two novel catalytic approaches for the chiral synthesis of alcohols from their chiral ketones utilized a co-factor regeneration procedure with two biomimics of the invention that do not contain the pyrophosphate nor the adenosine groups, namely 1-benzylnicotinamide triflate, (1a) and β-nicotinamide-5'-ribose methyl phosphate, (6). Their 1,4-dihydro derivatives were found to be recognized by the enzyme, horse liver alcohol dehydrogenase (HLADH), for catalyzed, highly enantiospecific conversions. Results are shown in FIG. 6.

Regioselective reduction of NAD$^+$, or compound (1) or (6) with in situ generated catalyst [Cp*Rh(bpy)H]$^+$ from rhodium catalyst precursor (2) in the presence of a hydride source, resulted in production of reduced biomimics, namely 1-benzyl-1,4-dihydronicotinamide (3), or 1,4-dihydronicotinamide-5'-ribose methyl phosphate (7), that are recognized by horse liver alcohol dehydrogenase (HLADH) to catalytically reduce ketones, such as phenethylmethyl ketone and benzylmethyl ketone, to corresponding chiral alcohols (>93% ee, S enantiomer).

Surprisingly, as already described above, biomimics recognition by HLADH (18) does not depend on the presence of the ribose, pyrophosphate, or adenosine groups. -HLADH recognizes compounds (1a)/(3) and (6)/(7) as hydride catalyst of the chiral conversion.

Tandem co-factor regeneration and chiral synthesis experiments with the novel biomimics (1) and (6), shown in FIG. 5, and NAD$^+$ used for a comparison, provided surprising results as seen in FIG. 7. The chiral ketone, PhCH$_2$CH$_2$C(O)CH$_3$ (12) in the presence of HLADH (18), was reduced to give the corresponding alcohol PhCH$_2$CH$_2$CH(OH)CH$_3$ (19), with >93% ee (S-enantiomer). Both biomimics (1) and (6), gave similar chiral synthesis results compared to NAD$^+$. After 24 hours, compounds (1), (6) and NAD$^+$ provided similar results. All gave >93% ee (S-enantiomer) and similar turnover frequencies, ~30 d$^{-1}$.

Clearly, all that is necessary for HLADH chiral recognition of the 1,4-NADH biomimics, (3) and (7), is the 1,4-dihydronicotinamide portion, while the 1-benzyl and ribose-5'-methyl phosphate role in binding in the hydrophobic pocket of HLADH does not affect the chiral transfer of hydride to ketone substrate.

A structure-reactivity study of the ketones further showed that benzylmethylketone, $PhCH_2C(O)CH_3$ (13) also provided the corresponding chiral alcohol, $PhCH_2CH(OH)CH_3$, (>99% ee, S-enantiomer), while acetophenone, $PhC(O)CH_3$ (14), was extremely slow in providing chiral product, $PhCH(OH)CH_3$, after 24 hours, yielding only 5% of product which was still >96% ee for the S-enantiomer. The results show that as the number of methylene groups is reduced (2 to 0) between the phenyl and carbonyl groups, the rate of chiral reduction is progressively slower showing that the specific non-covalent n-n interaction may be prevalent in the phenyl ketone binding site in proximity to a catalyst center in the enzyme.

Substrates for enzymatic reductions of ketones with biomimics described above are shown in FIG. 7.

FIG. 7 presents structures of ketone substrates 12–15 used for biomimic chiral synthesis of corresponding alcohols. Conversion of the substrates 12–15 to their corresponding alcohols are expressed in % yield, and TOF in $d^{-1}$ and S-enantiomer excess (ee) are also shown for each conversion. Corresponding values obtained with $NAD^+$ are given in parenthesis. The S-enantiomeric excess (ee) was determined by GLC with a modified β-cyclodextrin capillary column.

As seen in FIG. 7, the efficiency of the ketone to alcohol chiral conversion is almost identical to that of the efficiency of conversion catalyzed by $NAD^+$ for phenethylmethylketone (12), benzylmethylketone (13) and acetophenone (14). Somehow lower (yield in %) was found for compounds (14) and (15). TOF of each compound was very similar to the $NAD^+$ TOF (seen in parenthesis) as was the enantiomeric excess values obtained for these ketones under the same reaction conditions.

These results clearly show that the novel biomimics of the invention are efficient $NAD(P)^+/NAD(P)H$ replacement cofactors for $NAD(P)^+/NAD(P)H$ system in redox reactions.

The biomimics of the invention are further useful for derivatization of alcohols and for biomimetic reduction of norcamphor.

Figure 8:
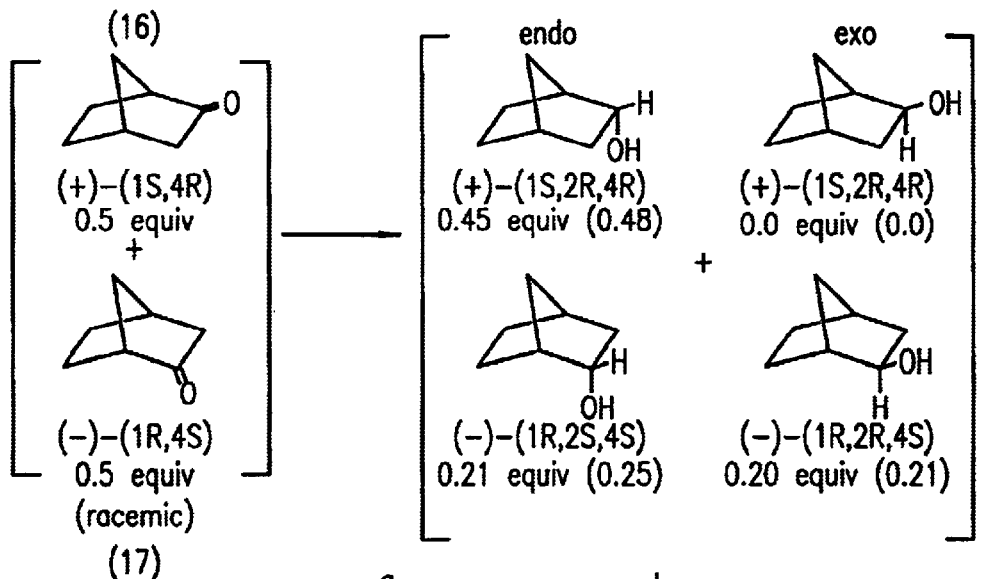
FIG. 8 shows biomimic reduction of norcamphor using biomimics of the invention.

FIG. 8 illustrates biomimetic reduction of norcamphor described in Example 9.

As seen in FIG. 8, the aliphatic ketone norcamphor, which is a commercial mixture of two enantiomers (16) and (17) reacted with the biomimics of the invention at different reduction rates and also provided a different diastereomeric mixture of predominantly endo chiral alcohols. As seen in FIG. 8, one enantiomer (17) gave an approximately equal mixture of exo and endo alcohols, while the enantiomer (16) gave exclusively the endo alcohol with exo alcohol not detected. Biomimic yield expressed in equivalent was 86% corresponding to $NAD^+$ yield of 94% under the same conditions.

The above results show, for the first time, that biomimic of the invention, structurally modified to retain the nicotinamide nucleus and either one similar substituent, ribose-5'-phosphate, 1-benzyl, or none, compared to $NAD^+$, can be converted to their 1,4-dihydronicotinamide derivatives using in situ generated $[Cp*Rh(bpy)H]^+$. These biomimics are recognized by enzymes such as dehydrogenases or oxidases for chiral synthesis of aryl substituted alcohols conversion of ketones and other oxido-reduction reactions.

The possible utilization of biomimics of the invention exemplarized by compounds (1) and (6) and their reduced forms (3) and (7), in biocatalytic processes is of industrial importance. Compound (1a), especially, is useful being more stable in acqueous/organic solvent under conditions that might cause $NAD^+$ to be hydrolytically compromised.

V. Device comprising biomimics for replacement of NAD(P)$^+$/NAD(P)H system

The efficient use of biomimics of the invention includes separation of products from the used enzyme and from regeneration catalytic systems. In nature, such separation is carried out by cell membranes. Consequently, one of the aspects of the current invention is to provide a device for replacement of $NAD(P)^+/NAD(P)H$ system and/or for regeneration of oxido-reduction catalyst described herein.

The device utilizes the same principles as those observed in nature. Typically, the device uses a membrane system comprising preferably a polymer matrix to confine regeneration biomimic compounds, catalysts and enzymes, as well as to provide control of pH, reaction conditions, mass transport and energy delivery. The catalyst precursors, preferably organorhodium catalyst precursors, the co-factors, preferably biomimic compounds of the invention, the enzyme(s), either oxidase or reductase or both, and/or any combination thereof, are tethered to a thin film polymer matrix in such a way that the rhodium catalyst precursor, biomimic compound and/or enzyme are confined within the polymer structure.

The device may be a biosensor or chemical membrane bioreceptor system, generally as described above, comprising at least two membranes placed around the solvent, the membranes limiting the transport of the co-factors, catalyst or enzymes but permitting the transport of oxygen or hydrogen ions.

Figure 9:
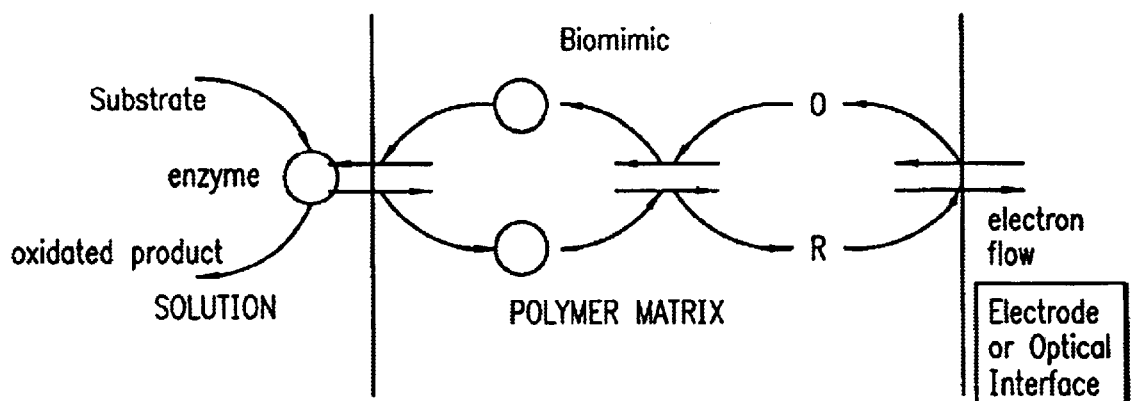
FIG. 9 shows a schematics of the device suitable for replacement or regeneration of NAD(P)$^+$/NAD(P)H system with biomimics of the invention, which may be used for biocatalysis or for manufacture of biosensors.

The general structure of the device is shown in FIG. 9, which consists of a source of electrons connected to an enzyme by means of a redox mediator (O/R), such as rhodium catalyst, ferrocene, phenones or other metal complexes capable of transferring electrons or hydride and a co-factor/biomimic, for example 1-benzylnicotinamide/1,4 dihydro-benzylnicotinamide or any other redox pair. The enzyme is responsible for carrying out the chemical reaction of interest.

The device permits regeneration of the co-factor in the desired redox form, prevents acid-base reactions which deactivate the co-factor and provides a suitable means of separation in order to avoid losses of co-factors in downstream processing.

VI. Utility of the co-factors

Typically, the preparation of natural $NAD(P)^+/NAD(P)H$ co-factors is very costly. To be at least somehow economic and practical, the co-factors must cycle many times. This invention discovered possible replacement of the expensive natural co-factors $NAD(P)^+/NAD(P)H$ with biomimic compounds that are equally or almost equally effective and are about a hundred times less expensive.

EXAMPLE 1

Methods and Materials

This example describes sources of materials, treatment of chemicals, instrumentation and method used.

Materials and Chemicals $[Cp*RhCl_2]_2$ was purchased from Colonial Metals and was used as received. $[Cp*Rh(bpy)(H_2O)]OTf_2$ was prepared according to the method described in *Oraganometallics*, 14:2806 (1995).

Concentrated solvents D$_2$O was purchased from Cambridge Isotope Laboratory and was degassed by bubbling argon through commercially supplied containers and stored under nitrogen for general use.

Ethyl ether was distilled over sodium benzophenone ketyl, and methylene chloride was distilled over calcium hydride under nitrogen prior to use.

Methanol was derived by treatment with Mg metal using the procedure given for super-dry ethanol.

All other solvents used were deoxygenated with argon or nitrogen prior to use.

β-Nicotinamide adenine dinucleotide (NAD$^+$, sodium salt), β-1,4-NADH(disodium salt), β-nicotinamide mononucleotide and reduced form of β-nicotinamide (disodium salt) and horse liver alcohol dehydrogenase (HLADH) were purchased from Sigma and were used without further purification. Water (HPLC grade), norcamphor (racemic) and sodium formate were purchased from Aldrich and were used without purification as received.

Pyridine (over calcium hydride), 3-picoline (over calcium hydride), ethyl ether (over sodium benzophenone ketyl), THF (over sodium benzophenone ketyl), and methylene chloride (over calcium hydride) were refluxed with proper drying agents in parentheses and distilled under nitrogen. Methanol (used for the syntheses of compound (3) and (7), was derived by treatment with Mg metal using the procedure given for super-dry ethanol. Benzyl chloride and benzyl bromide was distilled, and all other solvents used were deoxygenated with argon or nitrogen prior to use.

[CH$_3$)$_4$N]OTf was used as an internal standard in the NMR tube reactions.

GC-Chromatography

Unless otherwise specified, the GC chromatograms were obtained on a Hewlett Packard Instrument, model 8900A with an FID detector and a β-cyclodextrin column (Supelco: β-DEX-225, 30 m×0.32 mm×0.25 μm, nonbonded). The pH values were determined with an Orion 601A pH meter equipped with an Orion semimicro combination pH electrode. All reactions and manipulations were conducted under a nitrogen atmosphere in a Vacuum Atmospheres glovebox or by using Schlenk techniques.

Other carbonyl substrates and cyclohexanol used as an internal standard in the GC chromatography were purified by fractional distillation under argon and was deoxygenated prior to use. All of the commercially available optically pure alcohols were purchased from Fluka or Aldrich, and were used without further purification. The reduced product of benzyl acetone, PhCH$_2$CH$_2$CH(OH)CH$_3$, was obtained from the reaction of LiAl H4 with its corresponding ketone. Phenyl acetone, PhCH$_2$C(O)CH$_3$, was obtained by oxidation of its corresponding alcohol with pyridinium chlorochromate (PCC).

[Cp*Rh(bpy)(H$_2$O)]OTf$_2$, and NAD$^+$ models were prepared according to literature methods (*Angew. Chem. Inst. Ed. Enal.,* 29:388 (1990)).

NMR, UV and IR Spectra Recordation

Unless otherwise specified, NMR spectra were recorded on a Bruker AMX-300, AMX -400 or DRX-500 MHz spectrometer at room temperature.

The $^1$H NMR chemical shifts are expressed in ppm downfield from 2,2,3,3-d$_4$-3-trimethylsilyl propionate (sodium salt) and referenced to residual solvent resonances ($^1$H NMR:4.67 for D$_2$O), where the chemical shifts are given followed by multiplicity, coupling constants J in Hertz, integration in parentheses.

For complicated coupling patterns, such as δ(dt,J=3.2, 7.6, 1H), the doublet (d) represents the smaller coupling, and the triplet (t) indicates the larger coupling. Assignments are provided for key moieties only. The $^{31}$P{$^1$H} NMR chemical shifts were referenced to 85% H$_3$PO$_4$ (aq) as an external standard.

UV-vis spectra were measured with a Hewlett-Packard instrument model 8452A diode-array UV-vis spectrophotometa.

IR spectra were obtained on a Nicolet Instrument, model Impact 400 FT-IR spectrophotometer. Unless otherwise specified, IR samples were prepared in solid (KBr pellets) and absorptions are reported in wavenumbers (cm$^{-1}$). Electrospray/MS and FAB/MS spectra were acquired on a VG Quattro spectrometer and VG 70 spectrometer, respectively. The pH values were obtained with an Orion 601A pH meter equipped with an Orion semimicro combination pH electrode and those in D$_2$O were converted to pD (pH+0.4=pD). Elemental analyses were performed at the Department of Chemistry, University of California, Berkeley, Calif.

J. Young NMR tubes, featuring a resealable Teflon threaded cap, were pre-silylated with 1,1,1,3,3,3-hexamethyldisilazane to avoid acid catalyzed aquaphilic reactions. Unless otherwise noted, all reactions and manipulations were conducted under a nitrogen atmosphere in a Vacuum Atmospheres glovebox or by using Schlenk techniques.

[(CH$_3$)$_4$N]OTf and trimethyl phosphate were used as internal standards in NMR tube reactions for $^1$H and $^{31}$P{$^1$H} NMR, respectively.

EXAMPLE 2

Synthesis of 1-Benzylnicotinamide Type Biomimics

This example describes general procedure for syntheses of biomimic compounds of the invention, namely 1-benzylnicotinamide substrates (1a)–(1i).

Unless otherwise stated, the chloride or bromide salts of the substrates (1a)–(1i) were prepared by methods described in *JACS*, 77:2261 (1955)and *JACS*, 114:10134 (1992). THF was used as the reaction solvent to simplify the purification process (yields, 41–99%) Anion exchange was conducted either by utilizing AgOTf (1.0 equiv., in MeOH) or NaOTF (1.05 equiv, in acetone).

After solvent removal of the filtrate, the crude products were further purified by recrystallization from (acetone-CH$_2$CL$_2$=1)-Et$_2$O, followed by refrigeration at −15° C. The resulting crystals were collected on a glass-fritted funnel and washed with acetone Et$_2$O (1:4 at 0° C.), then were dried in vacuo over P$_2$O$_5$ in 86–97% yield.

General procedure used for preparation of the 1-benzylnicotinamide compounds is illustrated for biomimic compound (1d). Other compounds (1a–1i) are prepared in the same way, except that thionicotinamide is substituted with the appropriately substituted nicotinamide.

1-Benzylthionicotinamide, Triflate Salt (1d)

A 100 mL 2-necked Schlenk flask was equipped with a Claisen head equipped with a condenser and an addition funnel. The reaction unit was flame dried under vacuum and cooled to room temperature under nitrogen (N$_2$). Under a positive N$_2$ pressure, the thionicotinamide (2.82 g, 20 mmol) was added, followed by the addition of THF (40 mL) via syringe. The resulting suspension was then heated under gentle reflux to give a clear yellow solution. The benzyl chloride (2.53 g, 20 mmol) in 20 mL of THF was then placed in the addition funnel and added to the reaction flask dropwise over a period of 4 hours under $N_2$ with reflux. A yellow precipitate was observable when the addition was complete. The reaction mixture was allowed to reflux for another 4 hours under $N_2$, after which time the reaction flask was cooled in an ice-bath and the reaction mixture was further concentrated to two-thirds of the original volume on a high vacuum line. The precipitate was collected on a glass-fritted funnel and washed with acetone until there was no appreciable smell of thiols.

The collected yellow powder was further purified by three fractional recrystallizations from MeOH-$Et_2O$ at $-15°$ C. The resulting crystals were washed with acetone derived in vacuo over $P_2O_5$ to give the corresponding chloride salt (1.69 g) in 32% yield. Anion exchange was achieve by using NaOTf (1.05 equiv, in acetone) The crude product was further purified by two fractional recrystallizations from MeOH-$Et_2O$ at $-15°$ C., and the collected crystals were washed with acetone-$Et_2O$ (ratio=1:4, 0° C.) to give the title compound as yellow crystals in 84% yield.

$^1$H NMR ($D_2O$) δ9.31 (s, 1H, $H^2$ on Py), 8.88 (d, J=6.4, 1H, $H^6$ on Py), 8.71 (d, J=8.4, 1H), 8.00 (dd, J=6.0, 8.1, 1H), 7.41 (app s, 5H), 5.77 (s, 2H, —$CH_2Ph$); Anal. calcd for $C_{14}H_{13}F_3N_2O_3S_2$ (378.43): C, 44.43; H, 3.47; N, 7.40. Found: C, 44.36; H, 3.56; N, 7.65.

Spectroscopic and Analytical Data for Biomimics (1a)–(1i) 1-Benzylnicotinamide, Triflate Salt (a)

$^1$H NMR ($D_2O$) δ9.26 (s, 1H, $H^2$ on Py), 8.97 (d, J=6.1, 1H, $H^6$ on Py), 8.81 (d, J=8.1, 1H), 8.09 (app t, J=7.6, 1H), 7.42 (app s, 5H), 5.81 (s, 2H, —$CH_2Ph$); Anal. Calcd for $C_{14}H_{13}F_3N_2O_4S$ (362.36): C, 46.40; H, 3.62; N, 7.73. Found: C, 46.12; H, 3.65; N, 7.97.

1-Benzyl-N-methylnicotinamide, Triflate Salt (1b)

$^1$H NMR ($D_2O$) δ9.20 (s, 1H, $H^2$ on Py), 8.96 (d, J=5.8, 1H, $H^6$ on Py), 8.75 (d, J=8.2, 1H), 8.08 (app t, J=7.2, 1H), 7.43 (app s, 5H), 5.81 (s, 2H, —$CH_2Ph$), 2.88 (s, 3H); Anal. Calcd for $C_{15}H_{15}F_3N_2O_4S$ (376.39): C, 47.86; H, 4.03; N, 7.44. Found: C, 47.66; H, 4.35; N, 7.08.

1-Benzyl-N,N-diethylnicotinamide, Triflate Salt (1c)

$^1$H NMR ($D_2O$) δ8.97 (d, J=6.1, 1H, $H^6$ on Py), 8.95 (s, 1H, $H^2$ on Py), 8.54 (d, J=8.2, 1H), 8.10 (app t, J=6.9, 1H), 7.42 (app s, 5H), 5.79 (s, 2H, —$CH_2Ph$), 2.88 (s, 3H); Anal. Calcd for $C_{18}H_{21}F_3N_2O_4S$ (418.48): C, 51.66; H, 5.07; N, 6.70. Found: C, 51.88; H, 5.43; N, 6.89.

1-Benzyl-3-acetylpyridinium Triflate, (1e)

$^1$H NMR ($D_2O$) δ9.35 (s, 1H, $H^2$ on Py), 8.97 (d, J=6.6, 1H, $H^6$ on Py), 8.93 (d, J=8.0, 1H) 8.11 (app t, J=7.2, 1H), 7.40 (app s, 5H), 5.81 (s, 2H, —$CH_2Ph$), 2.65 (s, 3H); Anal. Calcd for $C_{15}H_{14}F_3NO_4S$ (361.37): C, 49.85; H, 3.91; N, 3.88. Found: C, 50.12; H, 3.57; N, 3.89.

1-Benzyl-3-carbomethoxypyridinium Triflate, (1f)

$^1$H NMR ($D_2O$) δ9.42 (s, 1H, $H^2$ on Py), 9.03 (d, J=6.1, 1H, $H^6$ on Py), 8.97 (d, J=8.1, 1H), 8.13 (dd, J=6.0, 8.1, 1H), 7.43 (app s, 5H), 5.83 (s, 2H, —$CH_2Ph$), 3.96 (s, 3H); Anal. Calcd for $C_{15}H_{14}F_3NO_5S$ (377.37): C, 47.74; H, 3.75; N, 3.71. Found: C, 48.10; H, 3.87; N, 3.99.

1-Benzyl-3-cyanopyridinium triflate, (1g)

$^1$H NMR ($D_2O$) δ9.42 (s, 1H, $H^2$ on Py), 9.17 (d, J=6.0, 1H, $H^6$ on Py), 8.90 (d, J=8.5, 1H), 8.22 (app t, J=7.2, 1H), 7.47 (app s, 5H), 5.87 (s, 2H, —$CH_2Ph$); Anal. Calcd for $C_{14}H_{11}F_3N_2O_3S$ (344.34): C, 48.83; H, 3.23; N, 8.14. Found: C, 48.85; H, 3.45; N, 8.56.

1-Benzyl-3-methylpyridinium triflate, (1h)

$^1$H NMR ($D_2O$) δ8.62 (s, 1H, $H^2$ on Py), 8.61 (d, J=5.0, 1H $H^6$ on Py), 8.25 (d, J=7.8, 1H), 7.81 (app t, J=7.2, 1H), 7.37 (app s, 5H), 5.64 (s, 2H, —$CH_2Ph$), 2.40 (s, 3H); Anal. Calcd for $C_{14}H_{14}F_3NO_3S$ (333.36): C, 50.44; H, 4.24; N, 4.20. Found: C, 50.01; H, 4.56; N, 4.64.

1-Benzyl-pyridinium triflate, (1i)

$^1$H NMR ($D_2O$) δ8.82 (d, J=5.9, 2H), 8.48 (app t, J=7.8, 1H), 7.98 (t, J=6.5, 2H), 7.42 (app s, 5H), 5.73 (s, 2H, —$CH_2Ph$); Anal. Calcd for $C_{13}H_{12}F_3NO_3S$ (319.33): C, 48.89; H, 3.80; N, 4.39. Found: C, 49.01; H, 3.78; N, 4.55.

N-(2 Hydroxyethyl) Nicotinamide Bromide Salt

N-(2 hydroxyethyl) nicotinamide bromide salt was prepared in the same fashion as N-benzylnicotinamide except that benzyl chloride was replaced with 2-chloroethanol.

EXAMPLE 3

Preparation of 1-Methylnicotinamide and 1-(P-Methoxybenzyl) Nicotinamide

This example describes preparation of 1-methylnicotinamide and 1-(p-methoxybenzyl) nicotinamide triflate salts.

1-Methylnicotinamide Triflate Salt

The iodide salt of 1-methylnicotinamide was prepared by the reaction of $CH_3I$ with the corresponding nicotinamide derivative. Nicotinamide (265.5 mg, 2.17 mmol) 2.17 mmol was placed in a 100 mL 2-necked Schlenk flask, equipped with a stirbar and a condenser, and then the Schlenk flask containing the solid mixture was degassed. The MeOH (6 mL, deoxygenated briefly) and $CH_3I$ (3mL, in excess) were added under $N_2$, respectively. The reaction flask was put in a 45° C. oil-bath and the reaction mixture was allowed to stir under $N_2$. The reaction was followed by TLC (EtOAC:$CH_2Cl_2$=3:1) as determined by the disappearance of nicotinamide. Generally, the reaction was complete within 6 hours. After cooling to room temperature, the precipitate was collected on a glass-fritted funnel, and washed with acetone (0° C.). The product was then dried in vacuo over $P_2O_5$ to afford the title compound (494.2 mg, 86%) as a pale-yellow powder.

Anion exchange was achieved by utilizing NaOTf (1.0 equiv, in acetone). The crude product was further purified by recrystallization from acetone-$Et_2O$ at $-15°$ C. to afford the title compound in >90% yield.

$^1$H NMR ($D_2O$) δ9.19 (s, 1H, $H^2$ on Py), 8.88 (d, J=6.0, 1H, $H^6$ on Py), 8.80 (d, J=8.7, 1H), 8.10 (app t, J=7.1, 1H), 4.39 (s, 3H, $CH_3$); Anal. Calcd for $C_8H_9F_3N_2O_4S$ (286.26): C, 33.56; H, 3.18; N, 9.79. Found: C, 33.80; H, 3.23; N, 10.02.

1-(p-Methoxybenzyl)nicotinamide, Triflate Salt $^1$H NMR ($D_2O$) δ9.21 (s, 1H, $H^2$ on Py), 8.93 (d, J=6.0, 1H, $H^6$ on Py), 8.78 (d, J=8.1, 1H), 8.07 (app t, J=7.2, 1H), 7.38 (d, J=8.6, 2H), 6.95 (d, J=8.6, 2H), 5.72 (s, 2H, —$CH_2Ph$), 3.73 (s, 3H, —$OCH_3$); Anal. Calcd for $C_{15}H_{15}F_3N_2O_5S$ (392.39); C, 45.91; H, 3.86; N, 7.14. Found: 46.00; H, 3.88; N, 7.34.

EXAMPLE 4

Preparation of β-Nicotinamide Ribose-5' Methyl Phosphate

This example describes preparation of the novel replacement biomimic β-nicotinamide ribose-5' methyl phosphate and compound (6).

β-Nicotinamide mononucleotide (502.9 mg, 1.44 mmol), dimethylaminopyridine (DMAP) (17.6 mg, $1.44 \times 10^{-1}$ mmol) and a stirbar were placed in a 250 mL flame-dried Schlenk flask. Standard Schlenk techniques were then performed to deoxygenate the solid mixture, and methanol (125 mL, dried) was added via cannula to dissolve the solids under $N_2$. Under positive $N_2$ pressure, 1,3-dicyclohexylcarbodiimide (DCC) (635.0 mg, 3.08 mmol) was added in one portion to the reaction mixture and the resulting solution was stirred at room temperature. The reaction progress was followed by TLC ($SiO_2$, MeOH—$CH_2Cl_2$=3, $R_f$=~0.3). After 3 hours, additional 1,3-dicyclohexylcarbodiimide (655.8 mg, 3.18 mmol) was added, and the reaction mixture was allowed to stir for another 24~30 hours.

The white precipitate was filtered on a glass-fritted funnel and washed with $CH_2Cl_2$ (2×5 mL). The collected filtrate was concentrated on a high vacuum line to give an oily residue. The mixture was then taken up with $H_2O$ (~1.5 mL, deoxygenated) and any insoluble species was further filtered off and rinsed with $CH_2Cl_2$ (2 mL). The solvent of the filtrate was stripped and a small amount of eluting solvent was used to dissolve the obtained residue. The mixture was then purified by column chromatography (column diameter, 20 mm; column height, 40 cm) with $SiO_2$ ($CH_3OH$—$CH_2Cl_2$=3,deoxygenated) under $N_2$. The eluant was derived on a high vacuum line to give a gummy residue, which can be solidified by the addition of a small amount of $CH_2Cl_2$, followed by removal of the solvent on a high vacuum line to yield the title compound dried in vacuo over $P_2O_5$ as a white solid (260.8 mg, 52%), or can be solidified upon sitting at −15° C. The title compound appears to be light-sensitive and somewhat air-sensitive. Storing the biomimic compound (6) at low temperature under subdued room light is highly recommended before use.

$^1$H NMR ($D_2$) δ9.35 (s, 1H, $H^2$ on Py), 9.16 (d, J=6.3, 1H, $H^6$ on Py), 8.87 (d, J=8.1, 1H), 8.19 (dd, J=6.3, 8.1, 1H), 6.11 (d, J=5.1, 1H, $H^{1'}$), 4.53 (m, 1H), 4.43 (t, J=5.1, 1H), 4.33 (dd, J=2.7, 5.1, 1H), 4.21 (ddd, J=2.5, 4.4, 12.1, 1H), 4.04 (ddd, J=2.3, 5.1, 12.1, 1H), 3.46 (d, $^3J_{HP}$=10.8, 3H, —$CH_3$); $^{31}$P{$^1$H} NMR (202.3 MHz, ($D_2$O) δ0.31; Anal. Calcd for $C_{12}H_{17}N_2O_8PO.1H_2O.0.1CH_3OH$ (353.29): C, 41.13; H, 5.03; N, 7.93. Found: C, 41.14; H, 5.13; N, 7.46.

Other biomimics of β-nicotinamide ribose-5-methyl phosphate-type are prepared in the same way except that methylation is substituted with alkylation or other appropriate reaction to attack polymers.

EXAMPLE 5

Preparation of Rhodium Catalyst Precursor

This example describes preparation of rhodium comprising catalyst precursor [Cp*Rh($\eta^2$-(N,N)-2,2'-bipyridyl)($H_2O$)](OTf)$_2$.

In a 50 mL Schlenk flask, equipped with a stirbar, was placed [Cp*Rh($H_2O$)$_3$]OTf$_2$ (200.0 mg, $338.78 \times 10^{-3}$ mmol), 2,2'-bipyridyl (53.1 mg, $339.97 \times 10^{-3}$ mmol) was added, and then the flask was capped with a septum. Standard Schlenk techniques were then performed to deoxygenate the solid mixture, and then $H_2O$ (4 mL, deoxygenated) was added via syringe through the septum under $N_2$ to give a suspension. The reaction mixture was allowed to stir at room temperature under $N_2$.

Generally, the reaction was complete within 4 hours as determined by the disappearance of the bipyridyl ligand, and by the presence of a clear yellow-orange solution. Any insoluble species were filtered off with a glass-fritted funnel through a 1-inch Celite bed via canula. The filter cake was washed with a small amount of $H_2O$ (deoxygenated) until the filter cake was colorless, and the solvent of the filtrate was removed on a high vacuum line to give a yellow powder. The resulting powder was further purified by recrystallization from hot $H_2O$ under $N_2$ followed by refrigeration at −15° C. The crystals were collected and washed with $CH_2Cl_2$-$Et_2O$ (ration=1, 0° C.), and were dried in vacuo over NaOH to give 2 (185.0 mg, 77%) as a yellow orange solid. The title complex is stable as a solid in the air.

$^1$H NMR ($D_2O$) δ9.04 (d, J=4.6, 2H, $H^6$ on Py), 8.39 (d, J=7.3, 2H), 8.24 (t, J=7.4, 2H), 7.83 (app t, J=6.6, 2H), 1.61 (s, 15H); IR 3085, 2914, 1604 (cm$^{-1}$); Anal. calcd for $C_{22}H_{25}F_6N_2O_7RhS2.H_2O$ (728.56): C, 36.27; H, 3.74; N, 3.85. Found: C, 36.30; H, 3.62; N, 4.14. Suitable single crystals for X-ray diffraction analysis were obtained by recrystallization from MeOH-$Et_2O$ at 15° C.

Other catalyst precursors are prepared in substantially the same way by substituting the rhodium with zinc, cobalt, nickel, iridium or ruthenium.

EXAMPLE 6

Synthesis of 1,4-Dihydronicotinamide Derivatives

This example describes general procedure useful for preparation of reduced derivatives, namely 1,4-dihydronicotinamides, of the biomimic compounds (1a)–(1i).

The 1,4-dihydronicotinamide derivatives were prepared according to the methods described in JACS, 114:10134 (1992). The synthesis of 1,4-dihydronicotinamide (3) was used as an example of other 1,4-dihydro reduced derivatives.

In a 25 mL Schlenk flask equipped with a stirbar was placed the chloride salt of the biomimic (1a) (27.7 mg, $111.37 \times 10^{-3}$ mmol) and $Na_2CO_3$ (38.7 mg, $365.1 \times 10^{-3}$ mmol), and $Na_2S_2O_4$ (71.9 mg, $342.75 \times 10^{-3}$ mmol) under $N_2$ were added. Then $H_2O$ (3 mL, deoxygenated) was added to the reaction flask via syringe, and the reaction mixture was heated in a 45° C. oil-bath for 10 min, after which, yellow oily drops were deposed on the wall of the reaction flask. The reaction flask was then cooled in an ice-bath, and the solvent was pipeted off under a positive $N_2$ pressure. The resulting oily residue was washed with $H_2O$ (1 mL×5, deoxygenated) and the washings were pipeted off under $N_2$. The residual water of the obtained oil was further removed azeotropically with $CH_2CL_2$ (5 mL×2) on a high vacuum line to give the corresponding 1,4-dihydropyridine derivative as a pale-yellow solid (yield, 78%). $^1$H NMR (CDCl$_3$) δ7.38~7.20 (m, 5H), 7.14 (d, J=1.6, 1H, $H^2$ on Py), 5.72 (qd, J=1.6, 8.1, 1H, $H^6$ on Py), 5.35 (br s, 2H, —$NH_2$), 4.73 (td, J=3.5, 8.1, 1H, $H^5$ on Py), 4.27 (s, 2H, —$CH_2$Ph), 3.15 (dd, J=1.6, 3.5, 2H, $H^4$ on Py); $^1$H NMR ($D_2$O-THF-d$_8$) δ7.60~7.45 (m, 5H), 7.35 (s, 1H, $H^2$ on Py), 6.01, (d, J=8.1, 1H, $H^6$ on Py), 4.94, (td, J=3.6, 8.1, 1H, $H^5$ on Py), 4.54 (s, 2H, —$CH_2$Ph), 3.28 (br s, 2H, $H^4$ on Py).

In most cases, the 1,4-dihydropyridine derivatives were isolated by the above stated procedure as pure compounds. However, in some cases, such as reduced biomimics (1c), (1d), and (1e) fractional recrystallization was required in order to obtain pure products.

EXAMPLE 7

Preparation of β-1,4-Dihydronicotinamide Ribose-5'-Methyl Phosphate

This example describes preparation of the reduced derivative of biomimic (6), namely β-1,4-dihydronicotinamide ribose-5'-methyl phosphate.

The 1,4-dihydro form of β-nicotinamide mononucleotide (147 mg, 371×10$^{-3}$ mmol), p-dimethylaminopyridine (6.1 mg, 50×10$^{-3}$ mmol), pyridinium p-toluenesulfonate (53 mg, 211×10$^{-3}$ mmol) and a stirbar were placed in a 100 mL flame-dried Schlenk flask. Schlenk techniques were performed to deoxygenate the solid mixture, and methanol (40 mL, dried) was then added via cannula through septum under nitrogen. Under positive $N_2$ pressure, 1,3-dicyclohexylcarbodiimide (209 mg, 1013×10$^{-3}$ mmol) was added in one portion to the reaction mixture and the resulting solution was stirred at room temperature under subdued room light. After 1 hour, additional pyridinium p-toluenesulfonate (53 mg, 211×10$^{-3}$ mmol) and 1,3-dicyclohexylcarbodiimide (261 mg, 1265×10$^{-3}$ mmol) were added, and the resulting mixture turned slightly cloudy. The reaction mixture was allowed to stir for another 7 hours to complete the reaction. TLC analysis of the final reaction mixture was conducted in a nitrogen-filled glovebox (Cellulose TLC: MeOH, Rf~0.4, $2^{nd}$ spot, streaking and highly fluorescent). After the removal of solvent on a high vacuum line, the residue was taken up with $H_2O$ (2.5 mL) in a glovebox and any insoluble species were filtered off and rinsed with a small amount of $CH_2C_2$(~2 mL×2). The solvent of the combined filtrate was stripped and a small amount of methanol was used to dissolve the obtained residue. The resulting mixture was then purified by column chromatography (column diameter, 20 mm; column height, 35 cm) with Sephadex LH-20 (MeOH, de-oxygenated) under nitrogen. The column separation of the mixture was monitored by a UV-vis detector to give the title compound co-eluting with sodium p-toluenesulfonate. The solvent of the collected eluant was removed on a high vacuum line and a pale yellow solid was obtained. According to $^1$H NMR spectroscopy and elemental analysis, the obtained pale yellow solid dried in a vacuo over $P_2O_5$ contains 0.33 mole of 6 ($C_{12}H_{18}O_8N_2PNa$, 372.28) and 0.67 mole of sodium p-toluenesulfonate, 6' ($C_7H_7O_3SNa$, 194.20) with a yield of 75% (222.2 mg, based on nicotinamide). The title compound is both light- and air-sensitive.

$^1$H NMR ($D_2O$) δ6.98 (s, 1H, $H^2$ on Py), 6.04 (d, J=8.3, 1H, $H^6$ on Py), 4.87 (td, J=3.4, 8.2, 1H, $H^5$ on Py), 4.77 (d, J=6.8, 1H $H^{1'}$), 4.16~4.09 (m, 2H), 3.97 (m, 1H), 3.82 (m, 2H, $H^{5'}$), 3.43 (d, $^3J_{HP}$=10.8, 2H, —$CH_3$), 2.92 (br s, 2H, $H^4$ on Py); $^{31}$P{$^1$H} NMR (161.9 MHz, $D_2O$) δ2.38; Anal. calcd for (0.33 6.0.67 6').0.4$H_2$O.0.$CH_3$OH (263.38, appr): C, 39.90; H, 4.54; N, 3.51; S, 8.16. Found: C, 39.56; H, 4.64; N, 3.57; S, 7.82.

Other reduced compounds were prepared in the same way.

EXAMPLE 8

$^1$H NMR Spectroscopy Mechanistic Studies on Reductions of the Novel Biomimics

This example describes $^1$H NMR spectroscopy studies of the novel biomimics.

In a typical reaction, a J. Young NMR tube was charged, biomimic substrates (1a)–(1i) (1.0 mol), 2 (1% mol), and $HCO_2Na$ (1.1 mol) used as the hydride source and a Schlenk techniques were conducted to deoxygenate the solid mixture. A diluted solvent was added to these solids for compounds (1a)–(1i), the solvent was $D_2O$-THF-d8 (1=1 0.75 mL, deoxygenated), and the NMR tube was placed in a liquid nitrogen bath. The contents were further degassed by two successive freeze-pump-thaw cycles. After thawing out the reaction mixture, the J. Young NMR tube was immediately put in a salted ice-bath and covered with aluminum foil. The reaction was then followed by $^1$H NMR spectroscopy at 26° C. temperature, after a speedy thawing out.

The given relative rates and turnover frequencies were determined by decreasing integration of the corresponding pyridinium salts measured against an internal standard, $(CH_3)_4N(OTf)$, during the first 2 h of the reaction. The ratios of the 1,4- and 1,6-dihydronicotinamide derivatives of compounds (1a), (1b) and (1d)–(1g) were obtained by comparison of the resonance signals with those of authentic samples, where the diagnostic signal is the resonance for —$CH_2Ph$ moiety which can be identified unambiguously in the $^1$H NMR spectrum.

Additionally, the signals of $H^2$ and $H^6$ protons on the pyridine ring of biomimic (7) or 1,4-NADH, were used for the isomer determination. It was further noticed that the signal for H4 biomimic (1) disappeared after a prolonged reaction time (>24 hours) and, in addition, the signal associated with the H4 protons of biomimic (3) also disappeared after >24 hours of reaction time. This was found to be a general phenomena for all biomimics that gave 1,4-dihydro products.

EXAMPLE 9

Kinetic and Thermodynamic Studies

This example describes studies producing kinetic and thermodynamic data for 1-benzylnicotinamide triflate (1a) performed in THF/$H_2O$, 1:1, β-nicotinamide -5'-ribose methyl phosphate (6) $H_2O$, pH=6.5, and NAD$^+$ performed in the regioselective reduction with [Cp*Rh(bpy)$H_2O$)][OTf]$_2$, 2 and in the presence of formate ion.

The kinetic experiments were carried out on a Hewlett Packard 8452A Diode Array Uv-Vis spectrophotometer, attached to a circulating water bath (VWR 1160). For experiments conducted at different temperatures, the circulating water bath, as well as the UV-vis instrument, were warmed up for at least an 1 hour before the kinic studies were initiated.

The 1-benzylnicotinamide triflate (1a) [CP*Rh(bpy)($H_2O$)][OTf]$_2$ (2) and 1-benzyl-1,4 dihydronicotinamide (3) were synthesized by methods as described in Examples 2, 4 and 7. The NAD$^+$ and 1,4-NADH compounds were purchased from Sigma and used as received. The THF was distilled from Na and deoxygenate with $N_2$ gas for 1 hour. Distilled water was purchased from Aldrich Chemical Co and deoxygenate prior to being used. A solution of THF/$H_2O$ (similar for 1:1 or 1:4 ratios) was used for all the kinetic experiments performed for compounds of 1-benzylnicotinamide type, unless otherwise specified. A stock solution of biomimic (1a) (0.018 M), 2 (6.23×10$^{-3}$ M), and sodium formate (0.25 M) were made for the kinetic experiments in THF/$H_2O$ (1:1).

A solution of 1-benzylnicotinamide triflate (1a), (4.29×10$^{-3}$ M) and sodium formate (0.0539) was made in a volumetric flask (10 mL) under $N_2$ in a THF/$H_2O$ (1:1) mixture. The different concentration of biomimic (1a) and sodium formate used for the kinetic experiments are reported above.

A 3.0 mL aliquot of this solution was transferred to a thermostated UV-vis cell by using an air-free syringe, which was also purged with $N_2$ gas. The sample was then brought to the desired temperature for 30–60 min in the UV-vis spectrophotometer thermostated cell holder. Then, 23 μL of a $6.23 \times 10^{-3}$ M stock solution of [CP*Rh(bpy)(H2O)]$^{2+}$ (2), was added-by syringe under a positive $N_2$ pressure, quickly mixed with the solution, and the absorbance increase at 354 nm was immediately recorded. The experiment was carried out for 2 hours and the formation of the product, 1-benzyl-1,4-dihydronicotinamide, (3) was followed, with the change in absorbance being recorded every 90 seconds. Some kinetic experiments were carried out until all the starting material was converted to product. The induced volume change was taken into account for the calculation of the turnover frequency (TOF).

The kinetic experiments for the β-nicotinamide-5'-ribose methyl phosphate (6) and natural NAD$^+$ were performed using the same general procedure described above. These kinetic experiments were carried out in $H_2O$ and the concentration of β-nicotinamide-5'-ribose methyl phosphate (6) or NAD$^+$, sodium formate, and [Cp*Rh(bpy)(H$_2$O)]$^{2+}$ (2), were in the order of $1.50 \times 10^{-3}$, 0.0186 M, and $1.42 \times 10^{-5}$ M, respectively. The $\lambda_{max}$ for the β-nicotinamide-5'-ribose methyl phosphate, (6), and natural NAD$^+$ was 336 nm. In all the initial rate plots, time =0 s was removed from the plots of Concentration versus Time. The standard deviation of the $r_i$ were calculated from 2σ values.

EXAMPLE 10

Enzymatic Reduction Catalyzed with Novel Biomimics

This example describes the general procedure used for enzymatic reduction of carbonyl substrates using biomimics of the invention as replacement for NAD$^+$ A. Enzymatic reduction of carbonyl substrates using NAD$^+$ as the cofactor

[Cp*Rh(bpy)(H$_2$O)]OTf$_2$ (1.9 mg, $2.61 \times 10^{-3}$ mmol), sodium formate (17.8 mg, $261.69 \times 10^{-3}$ mmol), NAD$^+$ (8.1 mg, $11.23 \times 10^{-3}$ mmol) and HLADH (10 units) were placed in a 10 mL Schlenk flask, and Schlenk techniques were followed to deoxygenate the solid mixture.

Under positive argon pressure, 5 mL of potassium phosphate buffer (100 mM, pH=7.02, deoxygenated) and carbonyl substrate ($83.58 \times 10^{-3}$ mmol, deoxygenated) were added via syringe. The reaction flask was immediately securely capped with a glass-stopper and shaken with a shaker in 30° C. water-bath. The reaction was monitored by gas chromatography (GC), equipped with a β-cyclodextrin column (Supelco, β-DEX-225), and the products were identified by comparing the retention time with the corresponding authentic chiral samples and were confirmed by GC-MS. The enantiomeric excess of the products was determined directly by their relative area in the chromatogram. The progress of the reaction was obtained by mixing the reaction aliquot with an internal standard (cyclohexanol in phosphate buffer), and then calibrating the measured relative area in the chromatogram with their corresponding response factors. The reaction was monitored for 24 hours.

B. Enzymatic reduction of carbonyl substrates using biomimics

The same procedure as described in section A was followed, except that NAD$^+$ was substituted with any one of the biomimic compounds of the invention.

C. Biomimetic reduction of norcamphor (racemic)

The procedure described in section A is equally applicable to reduction of racemic compounds such as norcamphor, seen in FIG. 8. The method requires the following modification. Due to the sublimation of norcamphor in vacuo, the addition of norcamphor was conducted under positive argon pressure, followed by the addition of phosphate buffer via syringe.

EXAMPLE 11

Biomimetic Reduction of 2-Pentanone

This example describes the procedure used for reduction of 2-pentanone.

The same procedure described in Example 10 was followed. The enantiomeric excess of the products was determined by derivatization of the alcohols with an optically pure S(−)-1-phenylethyl isocyanate in toluene at 140° C., followed by separation with a β-cyclodextrin column, as follows:

After 24 hours, the reaction mixture was extracted with $CH_2CL_2$ until there was no GC-detectable alcohols in the mother liquid. The combined extracts were dried with $Na_2SO_4$, followed by distilling off the solvent along with any residual water, which could be removed azeotropically with $CH_2Cl_2$, in an oil-bath under argon. The resulting residue was brought into a glove box, and 1.5 mL of toluene (CaH$_2$ dried) was used to make a solution, which was then transferred to a Schlenk tube. Excess of S(−)-1-phenylethyl isocyanate was then added to the above solution, and the Schlenk tube was sealed and brought out of the glove box. The reaction flask was put in a 140° C. oil-bath for 12~20 hours. The diastereomeric purity of the thus-formed diastereomers was determined by their relative area obtained in the chromatogram and was confirmed by authentic compounds and GC-MS.

What is claimed is:

1. A composition suitable for replacement of NAD(P)$^+$ NAD(P)H system in oxido-reduction enzymatic reactions, said composition comprising a compound of general formula (I), or a salt thereof, in a combination with its 1,4-reduced form compound (II)

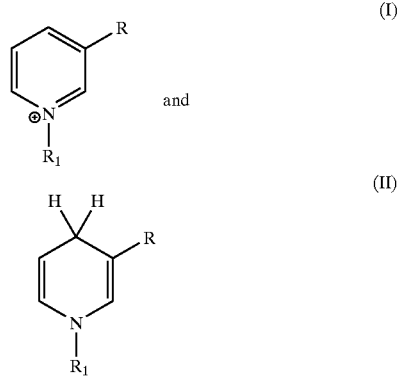

wherein R is —CN, —C(O)NH$_2$, —C(O)NHCH$_3$, —C(S)NH$_2$, —C(O)CH$_3$ or —C(O)OCH$_3$;

wherein $R_1$ is —(CH$_2$—(CH$_2$O)$_n$YR$_2$ or

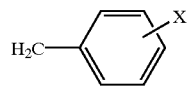

wherein Y is —OPOO—, —OBO$_2$—, —OSO$_2$—, CH$_3$NH—, —(CH$_2$)$_n$NH—, adenine, or imidazole;

wherein $R_2$ is H, CH$_3$, —(OCH$_2$CH$_2$)$_n$R$_3$, —(NCH$_2$CH$_2$)$_n$R$_3$ or —[—(N=P(OCH$_3$)$_2$]$_n$R$_3$;

wherein X is —OCH$_3$, —CF$_3$, —O(CH$_2$CH$_2$O)$_n$R$_3$ or —OPOOR$_3$;

wherein $R_3$ is H, or —CH$_3$;

wherein n is 1–2000.

2. The composition of claim 1 wherein the compound I is 1-(8-acryloyloxy-3,6-dioxaoctanoyl)-3-carbamoylpyridinium bromide salt and compound II is its reduced form.

3. The composition of claim 1 wherein the compound (I) in combination with its 1,4-reduced form is tethered to a polymer matrix.

4. The composition of claim 3 wherein the compound (I) or a compound (II), or both, are tethered to a polymer matrix.

5. The composition of claim 4 wherein the polymer matrix is selected from the group consisting of polyethyleneglycol (PEG), polyvinylglycol, polystyrene, polyalkylamine, polyphosphazene or polyethylene.

6. The composition of claim 5 wherein the polymer is polylalkylamine.

7. The composition of claim 6 wherein the polymer is PEG 200, PEG 400 or PEG 600.

8. The composition of claim 7 wherein the n is from 4 to 2000.

9. The composition of claim 8 wherein the n is from 4 to 10.

10. The composition of claim 1 wherein the salt of the compound (I) is a chloride, bromide, sulphate, phosphate or nitrate salt.

11. A method for replacement of NAD(P)$^+$/NAD(P)H system in oxido-reduction enzymatic reactions said method comprising a step of replacing NAD(P)$^+$/NAD(P)H co-factors with a biomimetic composition of claim 1.

12. The method of claim 11 further comprising a step of reacting a substrate to be oxidized or reduced in the presence of oxidase or reductase, and in the presence of the composition comprising an oxidized and reduced form of the biomimic and further in the presence of a catalyst or a catalyst precursor.

13. The method of claim 12 wherein the compound (I) or a compound (II), or both, are tethered to a polymer matrix.

14. The method of claim 13 wherein the polymer matrix is selected from the group consisting of polyethyleneglycol, polyvinylglycol (PEG), polystyrene, polyalkylamine, polyphosphazene or polyethylene.

15. The method of claim 14 wherein the polymer is polylalkylamine.

16. The method of claim 15 wherein the polymer is PEG 200, PEG 400 or PEG 600.

17. The method of claim 16 wherein the catalyst precursor provides a hydride.

18. The method of claim 17 wherein the catalyst is [Cp*Rh(bpy)(H$_2$O) ] triflate or a salt thereof.

* * * * *

UNITED STATES PATENT AND TRADEMARK OFFICE
CERTIFICATE OF CORRECTION

| | | |
|---|---|---|
| PATENT NO. | : 6,716,596 B2 | Page 1 of 2 |
| APPLICATION NO. | : 09/805726 | |
| DATED | : April 6, 2004 | |
| INVENTOR(S) | : Fish et al. | |

It is certified that error appears in the above-identified patent and that said Letters Patent is hereby corrected as shown below:

On the title page Item [75], the name "Christine H. Lo" should be --H. Christine Lo--;

In Fig. 1C, the footnote references "A" and "B" should be deleted, as they do not refer to any note in the text;

In Fig. 3, compounds 10 and 11 having a "-" charge indicated in the pyridyl ring structure should have a "+" charge instead;

Fig. 6 should be corrected as follows: In the Drawings insert what is being asked.
*FIG 6*

Make bond to -OH single

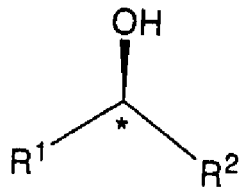

UNITED STATES PATENT AND TRADEMARK OFFICE
CERTIFICATE OF CORRECTION

PATENT NO. : 6,716,596 B2  Page 2 of 2
APPLICATION NO. : 09/805726
DATED : April 6, 2004
INVENTOR(S) : Fish et al.

It is certified that error appears in the above-identified patent and that said Letters Patent is hereby corrected as shown below:

Show 1,4 double bonds and delete + charge:

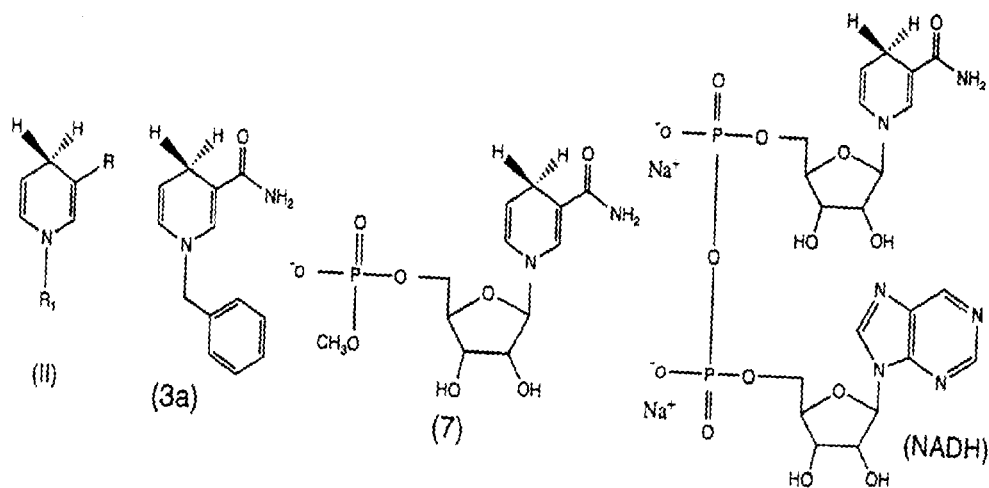

Signed and Sealed this

First Day of April, 2008

JON W. DUDAS
*Director of the United States Patent and Trademark Office*